(12) United States Patent
Mann

(10) Patent No.: US 11,445,971 B2
(45) Date of Patent: Sep. 20, 2022

(54) BRAINWAVE ACTUATED APPARATUS

(71) Applicant: INTERAXON INC., Toronto (CA)

(72) Inventor: Steve Mann, Toronto (CA)

(73) Assignee: INTERAXON INC., Toronto (CA)

( * ) Notice: Subject to any disclaimer, the term of this patent is extended or adjusted under 35 U.S.C. 154(b) by 0 days.

(21) Appl. No.: 16/774,545

(22) Filed: Jan. 28, 2020

(65) Prior Publication Data

US 2020/0163572 A1    May 28, 2020

Related U.S. Application Data

(63) Continuation of application No. 15/392,483, filed on Dec. 28, 2016, now Pat. No. 10,582,875, which is a
(Continued)

(51) Int. Cl.
| | |
|---|---|
| *A61B 5/00* | (2006.01) |
| *H04W 28/08* | (2009.01) |
| *H04W 88/02* | (2009.01) |
| *G06F 3/01* | (2006.01) |
| *G06F 3/0487* | (2013.01) |
| *A61B 5/375* | (2021.01) |
| *G05B 15/02* | (2006.01) |
| *A61B 5/374* | (2021.01) |
| *H04W 88/06* | (2009.01) |
| *G08B 7/06* | (2006.01) |

(52) U.S. Cl.
CPC ............ *A61B 5/375* (2021.01); *A61B 5/374* (2021.01); *A61B 5/6803* (2013.01); *G05B 15/02* (2013.01); *G06F 3/015* (2013.01); *G06F 3/016* (2013.01); *G06F 3/0487* (2013.01); *H04W 28/08* (2013.01); *H04W 88/02* (2013.01); *G08B 7/06* (2013.01); *H04W 88/06* (2013.01)

(58) Field of Classification Search
CPC ..... A61B 5/0482; A61B 5/048; A61B 5/6803; G05B 15/02; H04W 28/08; H04W 88/02; H04W 88/06; G06F 3/016; G06F 3/0487; G06F 3/015; G08B 7/06
See application file for complete search history.

(56) References Cited

U.S. PATENT DOCUMENTS

| | | |
|---|---|---|
| 4,013,068 A | 3/1977 | Settle et al. |
| 4,174,106 A | 11/1979 | Moser |

(Continued)

OTHER PUBLICATIONS

Palke, Amy, "Brainathlon: Enhancing Brainwave Control Through Brain-Controlled Game Play", 2004, http://citeseerx.ist.psu.edu/viewdoc/download?doi=1 0.1.1.89.8418&rep=rep1 &type=pdf.
(Continued)

*Primary Examiner* — Charles R Kasenge
(74) *Attorney, Agent, or Firm* — Norton Rose Fulbright Canada LLP

(57) ABSTRACT

A brainwave actuated apparatus has a brainwave sensor for outputting a brainwave signal, an effector responsive to an input signal, and a controller operatively connected to an output of said brainwave sensor and a control input to said effector. The controller is adapted to determine characteristics of a brainwave signal output by said brainwave sensor and based on said characteristics, derive a control signal to output to said effector.

16 Claims, 13 Drawing Sheets

Mind and body

Related U.S. Application Data continuation of application No. 13/154,022, filed on Jun. 6, 2011, now Pat. No. 9,563,273.

(60) Provisional application No. 61/351,725, filed on Jun. 4, 2010.

(56) References Cited

U.S. PATENT DOCUMENTS

| | | | |
|---|---|---|---|
| 4,211,409 A | 7/1980 | Nielsen | |
| 4,690,142 A | 9/1987 | Ross et al. | |
| 4,883,067 A | 11/1989 | Knispel et al. | |
| 4,949,726 A * | 8/1990 | Hartzell | A61B 5/0482 273/460 |
| 5,213,338 A | 5/1993 | Brotz | |
| 5,241,967 A * | 9/1993 | Yasushi | A61B 5/378 600/545 |
| 5,474,082 A * | 12/1995 | Junker | G06F 3/015 600/545 |
| 5,692,517 A * | 12/1997 | Junker | G16H 40/63 600/545 |
| 5,911,635 A | 6/1999 | Ogden | |
| 5,983,129 A | 11/1999 | Cowan et al. | |
| 5,994,853 A | 11/1999 | Ribbe | |
| 6,024,700 A | 2/2000 | Nemirovski et al. | |
| 6,071,229 A * | 6/2000 | Rubins | A61M 21/00 600/27 |
| 6,171,239 B1 | 1/2001 | Humphrey | |
| 6,254,536 B1 | 7/2001 | DeVito | |
| 6,259,889 B1 | 7/2001 | LaDue | |
| 6,349,231 B1 | 2/2002 | Musha | |
| 6,516,246 B2 | 2/2003 | Derakhshan | |
| 6,542,081 B2 | 4/2003 | Torch | |
| 6,609,017 B1 | 8/2003 | Shenoy et al. | |
| 6,636,763 B1 | 10/2003 | Junker et al. | |
| 6,695,885 B2 | 2/2004 | Schulman et al. | |
| 6,731,964 B2 | 5/2004 | Shenoy et al. | |
| 6,892,098 B2 * | 5/2005 | Ayal | A61N 1/36003 607/45 |
| 6,952,687 B2 | 10/2005 | Andersen et al. | |
| 7,187,968 B2 | 3/2007 | Wolf et al. | |
| 7,209,788 B2 | 4/2007 | Nicolelis et al. | |
| 7,647,097 B2 | 1/2010 | Flaherty et al. | |
| 7,881,780 B2 | 2/2011 | Flaherty | |
| 7,991,461 B2 | 8/2011 | Flaherty et al. | |
| 8,060,194 B2 | 11/2011 | Flaherty | |
| 8,095,209 B2 | 1/2012 | Flaherty | |
| 8,279,050 B2 | 10/2012 | Coombs | |
| 8,396,546 B2 | 3/2013 | Hirata et al. | |
| 8,519,841 B2 | 8/2013 | Fukuyori | |
| 8,519,950 B2 | 8/2013 | Radivojevic et al. | |
| 8,628,333 B2 | 1/2014 | Prinzel et al. | |
| 8,628,462 B2 * | 1/2014 | Berka | A61M 21/02 600/27 |
| 8,632,376 B2 | 1/2014 | Dooley et al. | |
| 2001/0056225 A1 | 12/2001 | DeVito | |
| 2002/0103429 A1 | 8/2002 | deCharms | |
| 2004/0073129 A1 * | 4/2004 | Caldwell | A61B 5/0478 600/544 |
| 2004/0156467 A1 | 8/2004 | Freifeld | |
| 2004/0267320 A1 | 12/2004 | Taylor et al. | |
| 2005/0090756 A1 | 4/2005 | Wolf et al. | |
| 2005/0283203 A1 | 12/2005 | Flaherty et al. | |
| 2006/0057549 A1 | 3/2006 | Prinzel et al. | |
| 2006/0061544 A1 | 3/2006 | Min et al. | |
| 2006/0122531 A1 | 6/2006 | Goodall et al. | |
| 2006/0167564 A1 * | 7/2006 | Flaherty | A61F 2/70 623/57 |
| 2006/0189899 A1 | 8/2006 | Flaherty et al. | |
| 2006/0229843 A1 | 10/2006 | Freifeld | |
| 2007/0016096 A1 | 1/2007 | McNabb | |
| 2007/0197292 A1 | 8/2007 | Collura et al. | |
| 2008/0082020 A1 | 4/2008 | Collura | |
| 2008/0143954 A1 | 6/2008 | Abreu | |
| 2008/0144854 A1 | 6/2008 | Abreu | |
| 2008/0161673 A1 | 7/2008 | Goodall et al. | |
| 2008/0200224 A1 | 8/2008 | Parks | |
| 2008/0236373 A1 | 10/2008 | Motsenbocker | |
| 2008/0287821 A1 | 11/2008 | Jung et al. | |
| 2009/0018407 A1 | 1/2009 | Jung et al. | |
| 2009/0024050 A1 | 1/2009 | Jung et al. | |
| 2009/0025023 A1 | 1/2009 | Pradeep et al. | |
| 2009/0051544 A1 * | 2/2009 | Niknejad | G06F 3/011 340/573.1 |
| 2009/0081923 A1 | 3/2009 | Dooley et al. | |
| 2010/0010289 A1 * | 1/2010 | Clare | A61M 21/02 600/27 |
| 2010/0016753 A1 | 1/2010 | Firlik | |
| 2010/0068146 A1 | 3/2010 | Luther-Forsstrom et al. | |
| 2010/0087701 A1 * | 4/2010 | Berka | A61M 21/02 600/27 |
| 2010/0094156 A1 | 4/2010 | Collura | |
| 2010/0192754 A1 | 8/2010 | Kim et al. | |
| 2010/0259472 A1 | 10/2010 | Radivojevic et al. | |
| 2010/0285440 A1 | 11/2010 | Parikh et al. | |
| 2010/0315262 A1 | 12/2010 | Coombs | |
| 2011/0009193 A1 | 1/2011 | Bond et al. | |
| 2011/0015539 A1 | 1/2011 | deCharms | |
| 2011/0054240 A1 * | 3/2011 | Bender | A61M 21/02 600/27 |
| 2011/0054242 A1 | 3/2011 | Bender | |
| 2011/0084795 A1 | 4/2011 | Fukuyori | |
| 2011/0270074 A1 | 11/2011 | deCharms | |
| 2013/0303837 A1 * | 11/2013 | Berka | A61B 5/369 600/28 |

OTHER PUBLICATIONS

USPTO, Office Action for U.S. Appl. No. 15/392,483 dated May 16, 2018.

USPTO, Office Action for U.S. Appl. No. 15/392,483 dated Feb. 14, 2019.

USPTO, Office Action for U.S. Appl. No. 15/392,483 dated Jul. 2, 2019.

USPTO, Office Action for U.S. Appl. No. 13/154,022 dated Jan. 24, 2014.

USPTO, Office Action for U.S. Appl. No. 13/154,022 dated Oct. 29, 2014.

USPTO, Office Action for U.S. Appl. No. 13/154,022 dated Mar. 4, 2015.

USPTO, Office Action for U.S. Appl. No. 13/154,022 dated Oct. 8, 2015.

USPTO, Office Action for U.S. Appl. No. 13/154,022 dated Apr. 12, 2016.

* cited by examiner

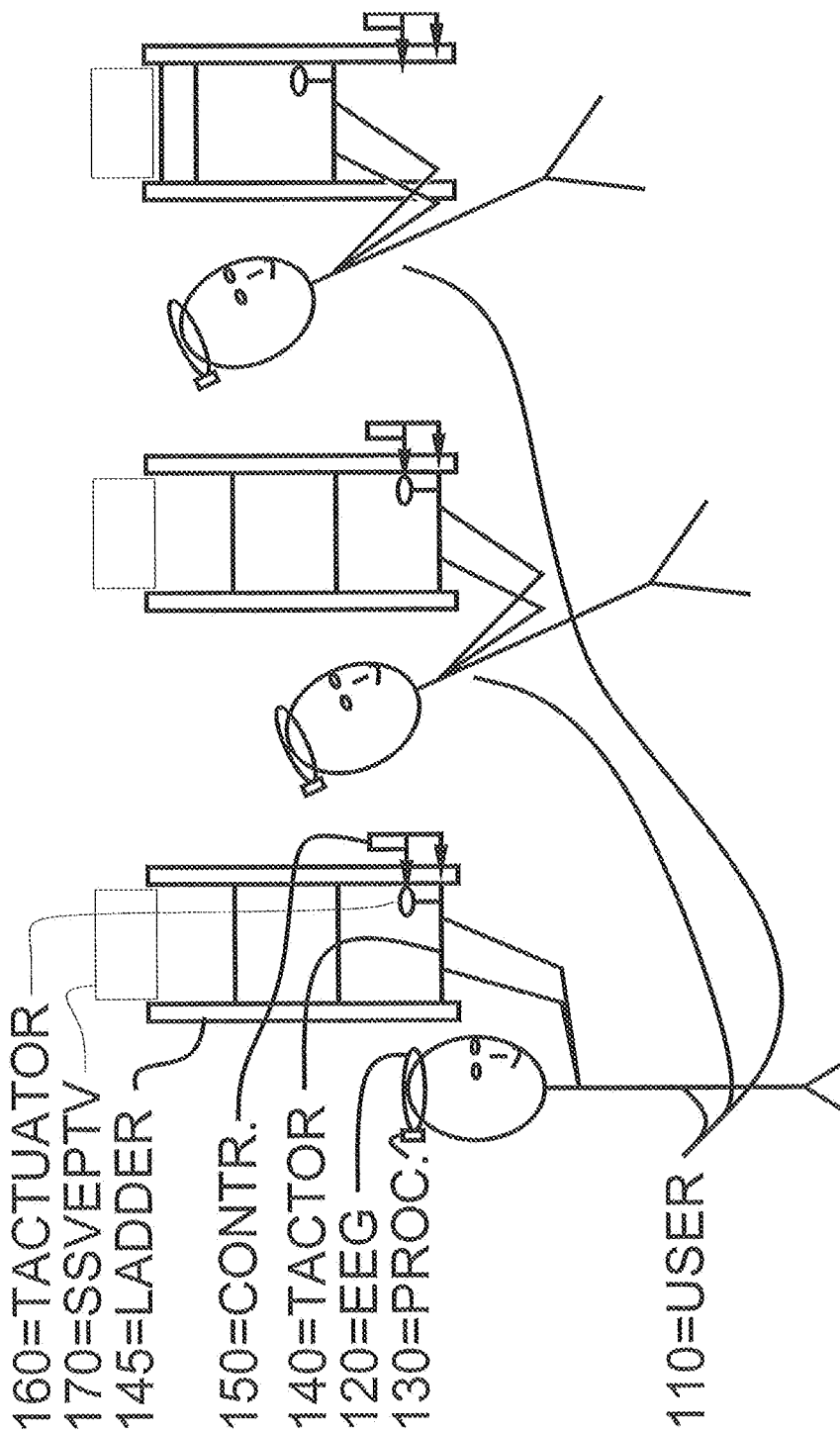
FIG. 1: Mind and body

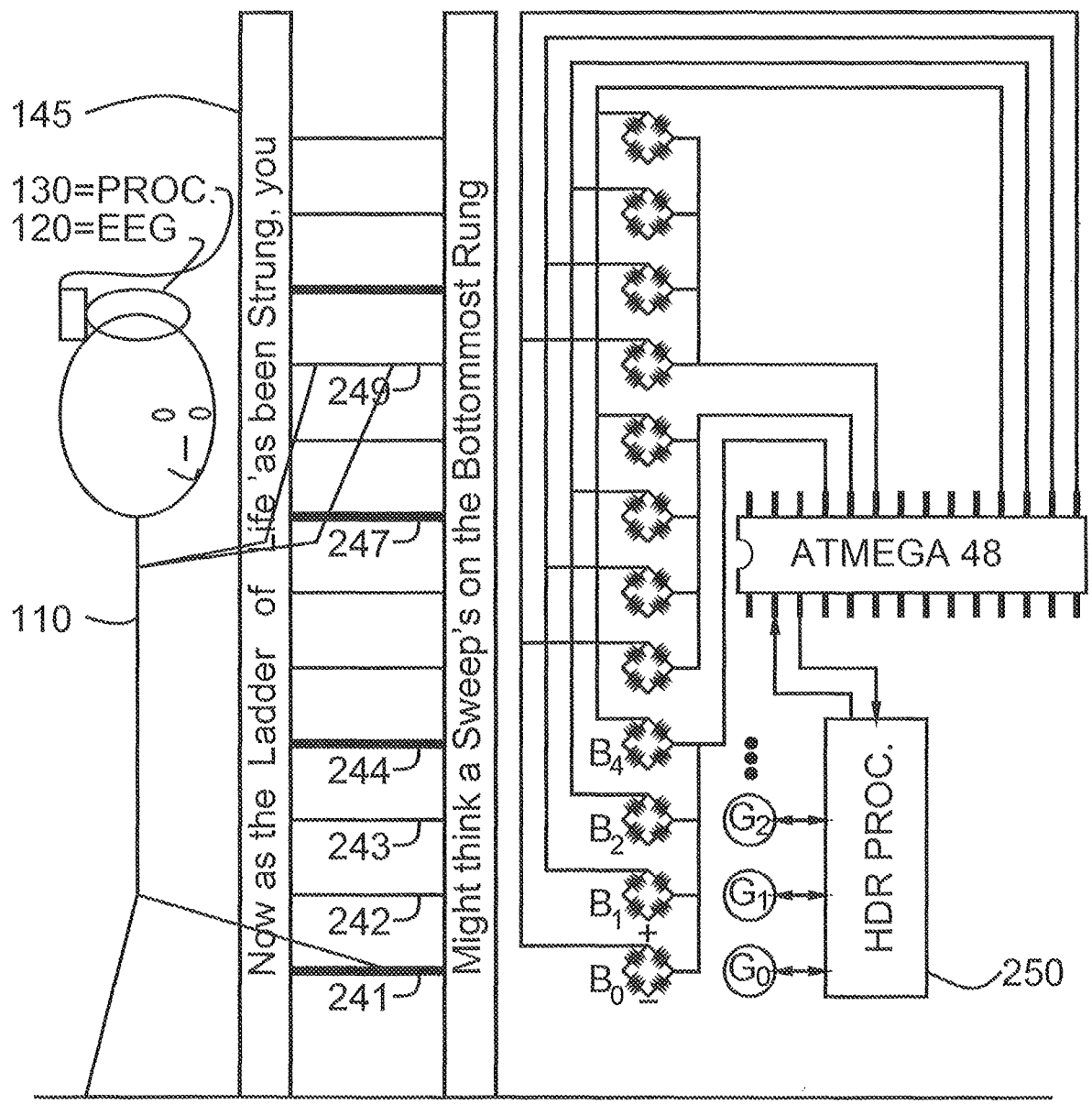
Fig. 2: Ladder of Life

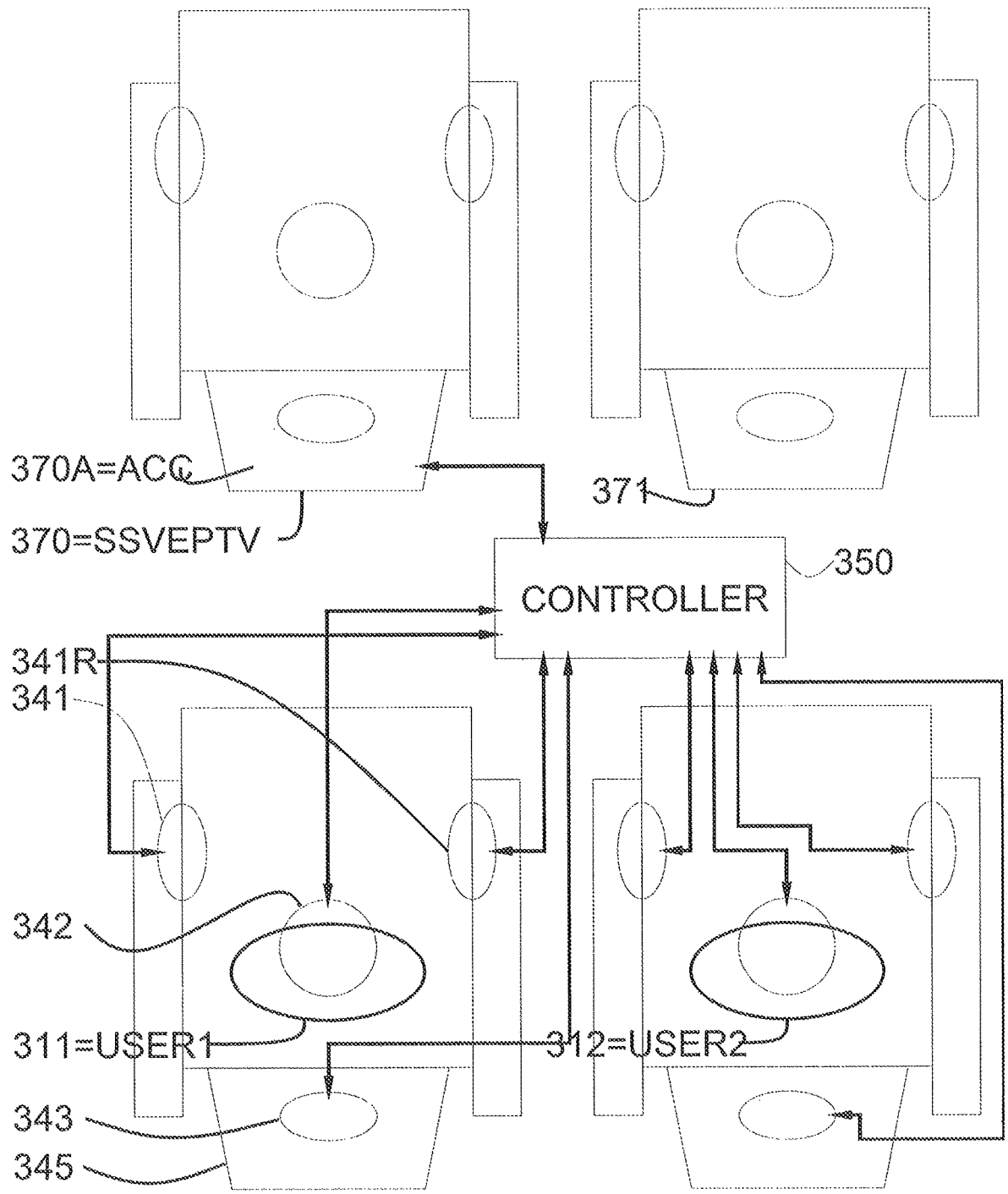
FIG. 3: In-flight entertainment, etc.

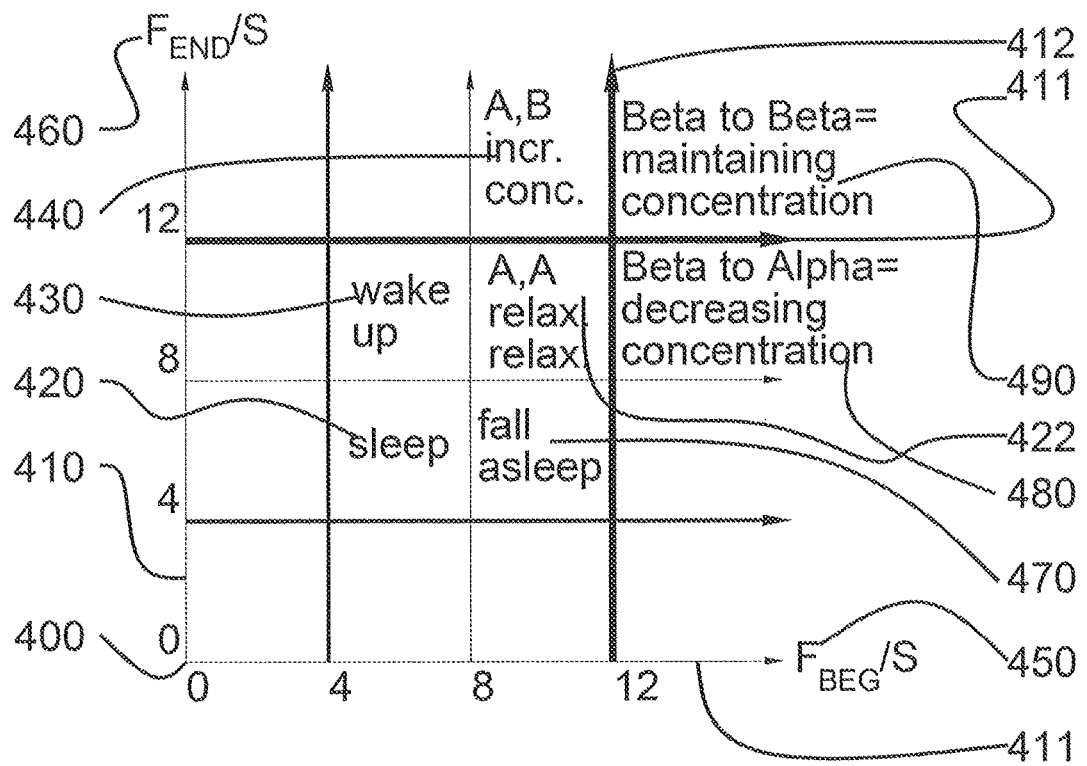
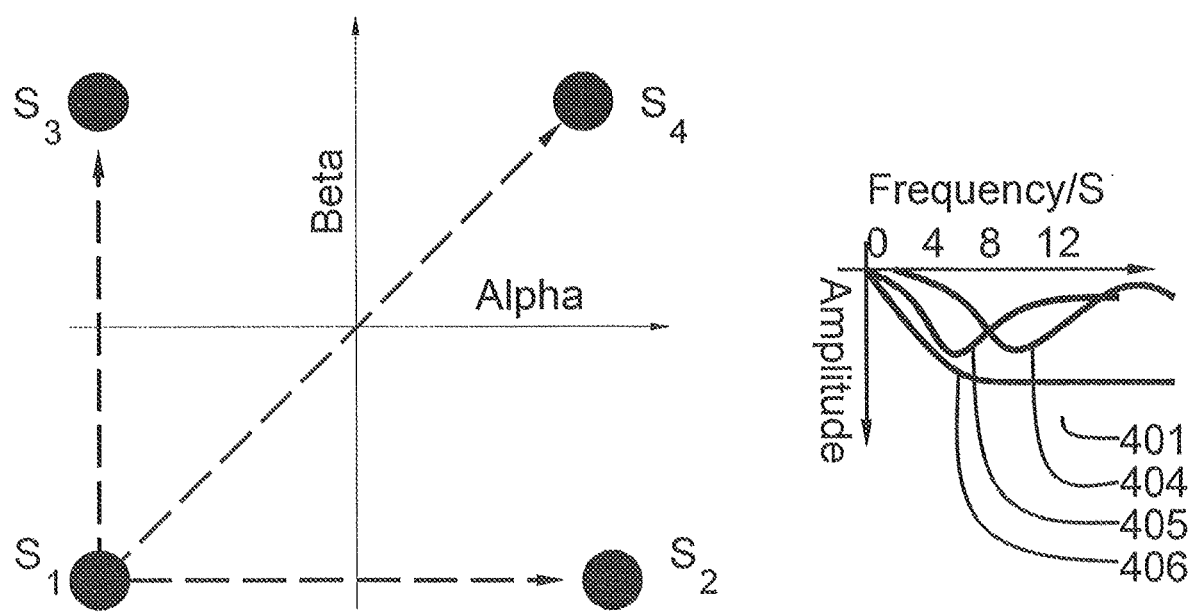
FIG. 4: Chirplet Transform and brain states

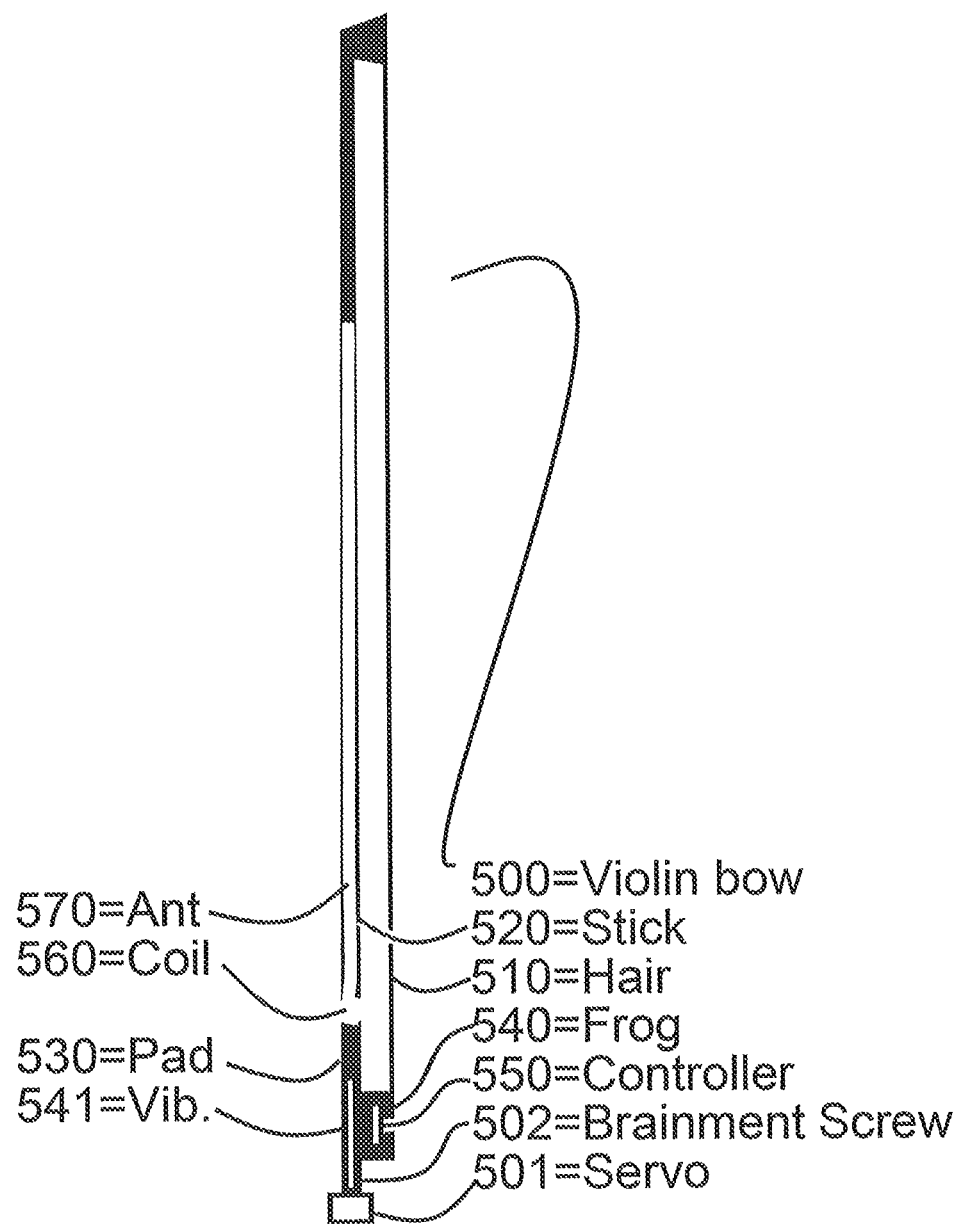
Fig. 5, Thought-controlled Technology

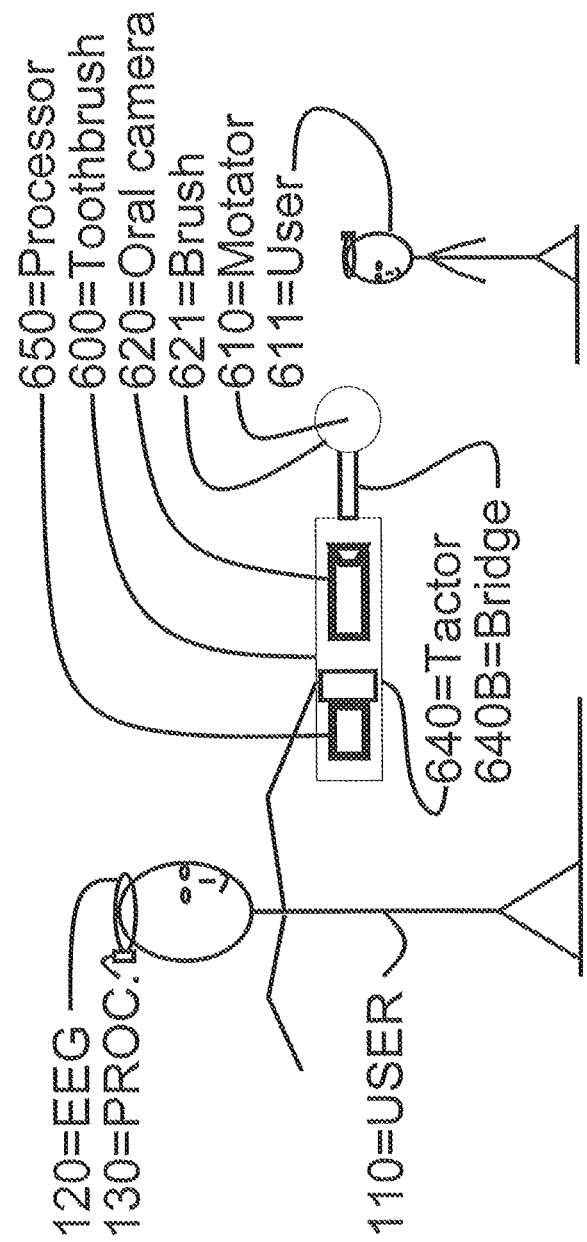
FIG. 6a: Toothbrush: Parent and child

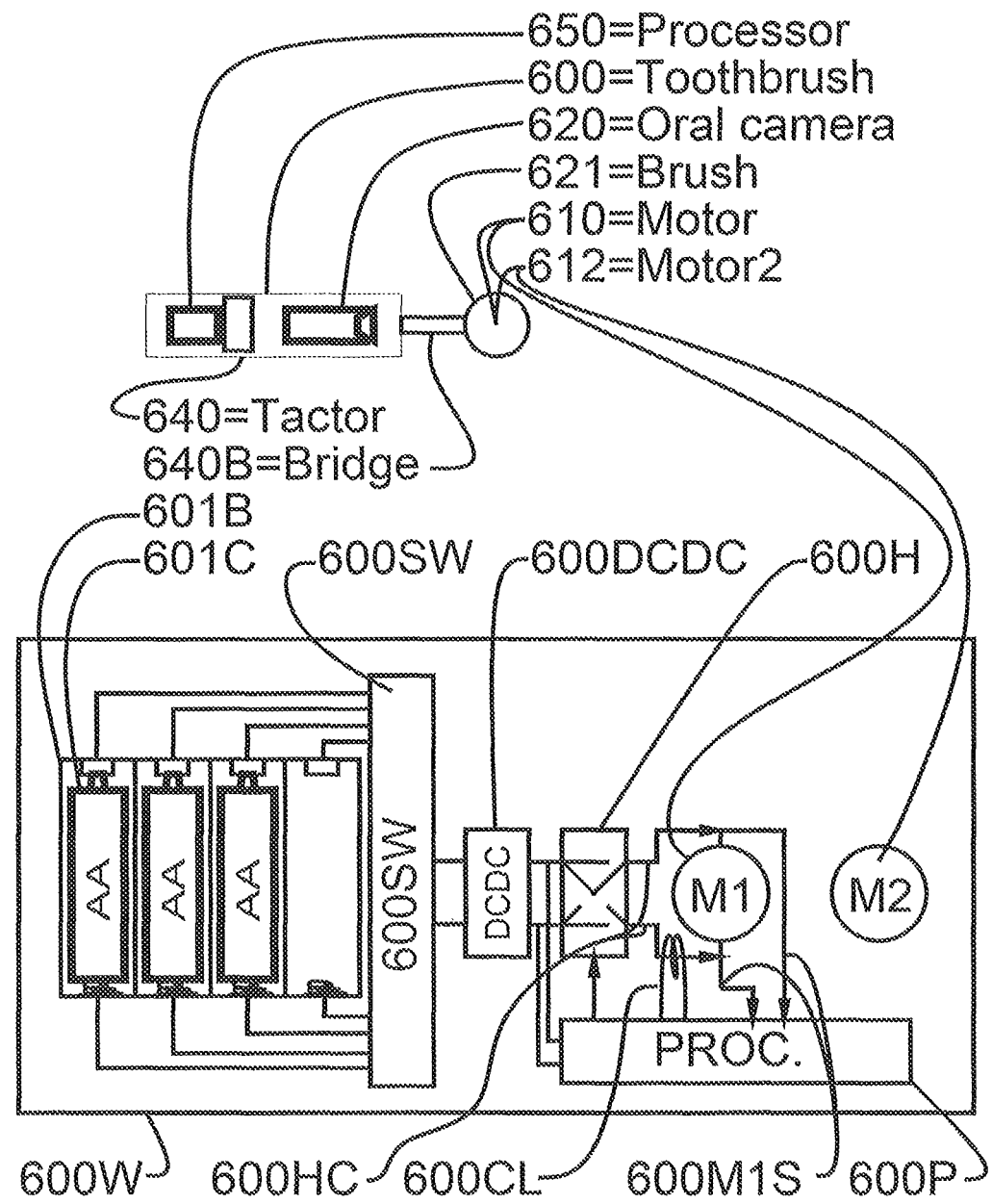
FIG. 6b: Multimotor tactile synthesizer

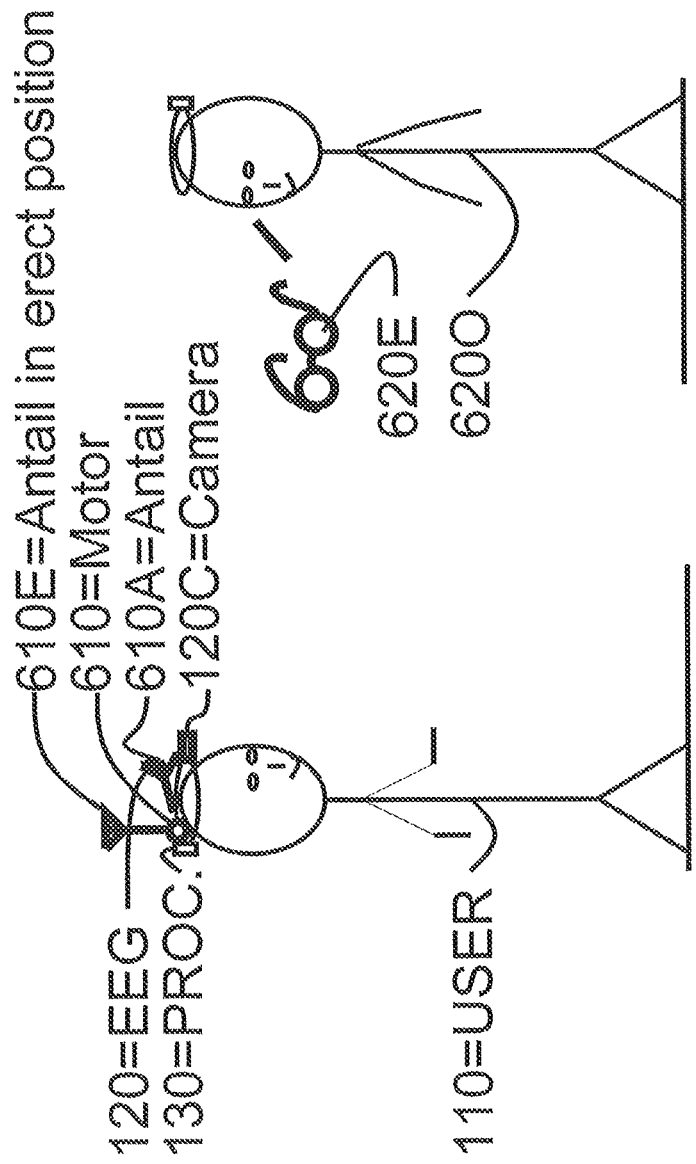
FIG. 6c: Antail TM antenna tail

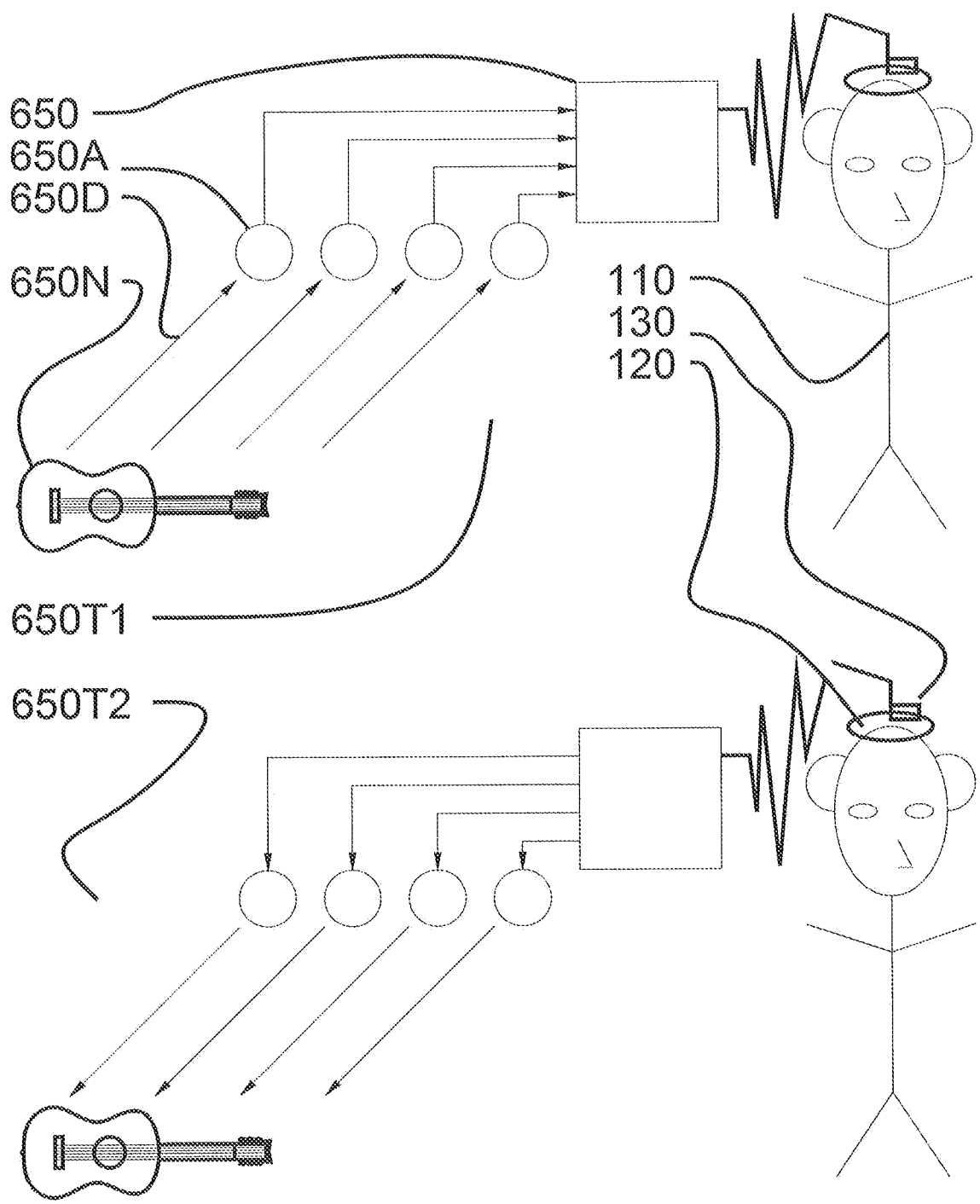
FIG 6d: Expression of annoyance

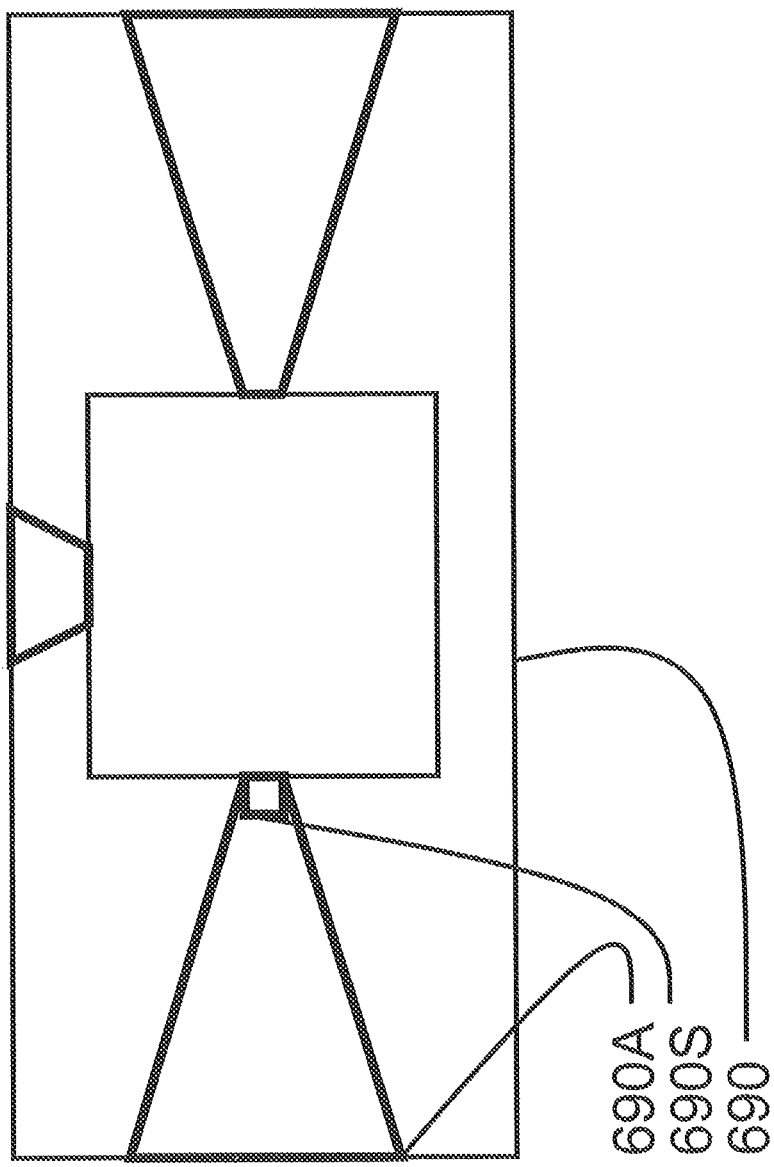
FIG. 6e: Vehicular embodiment

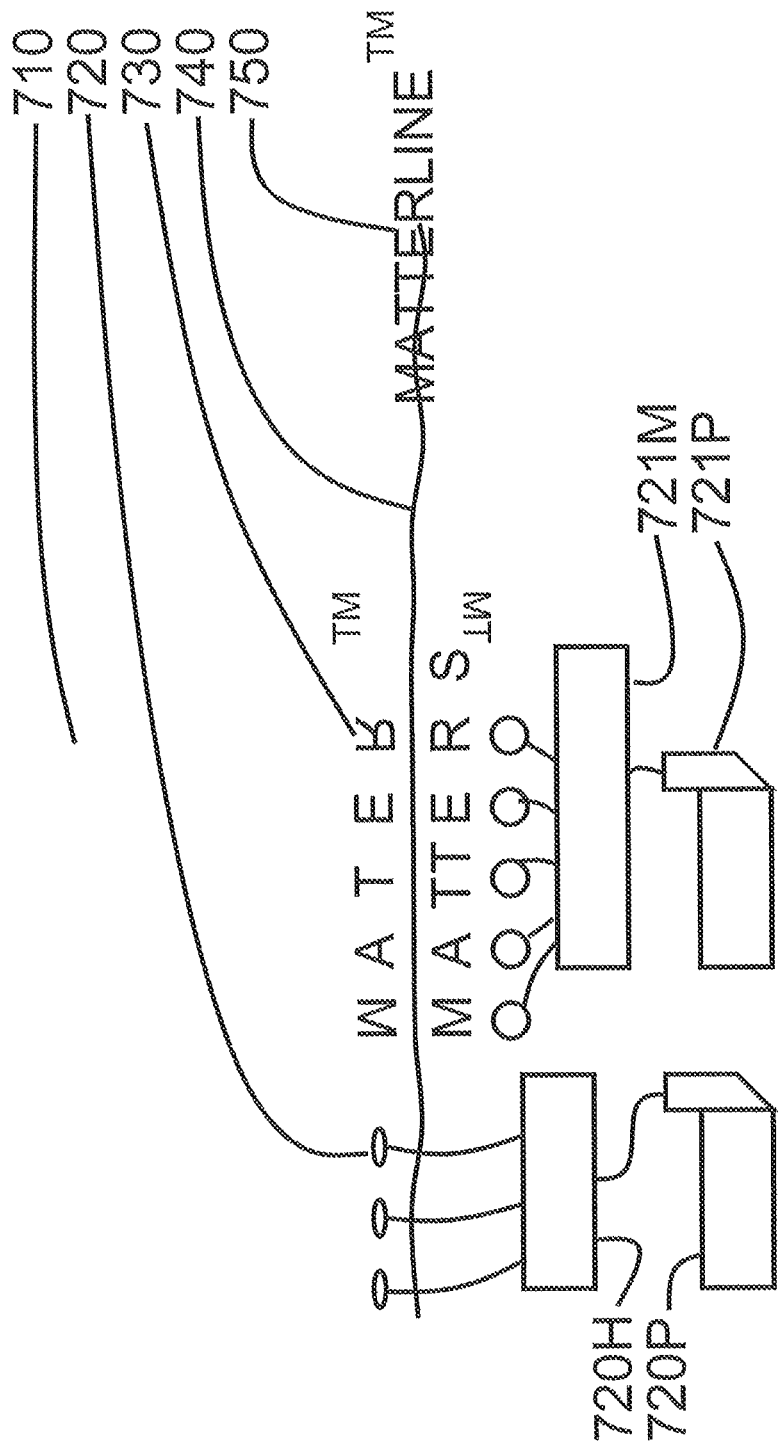
FIG. 7: Hot tub and corporate logo entrainment

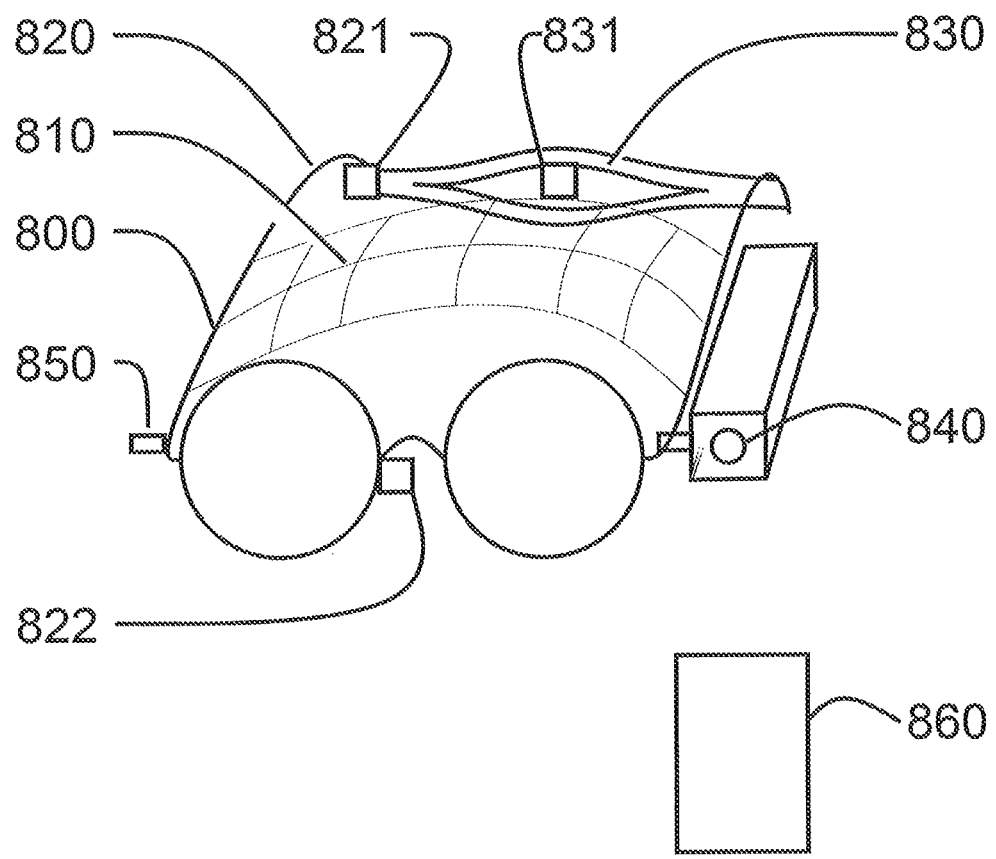
FIG. 8: ThinkingCap™

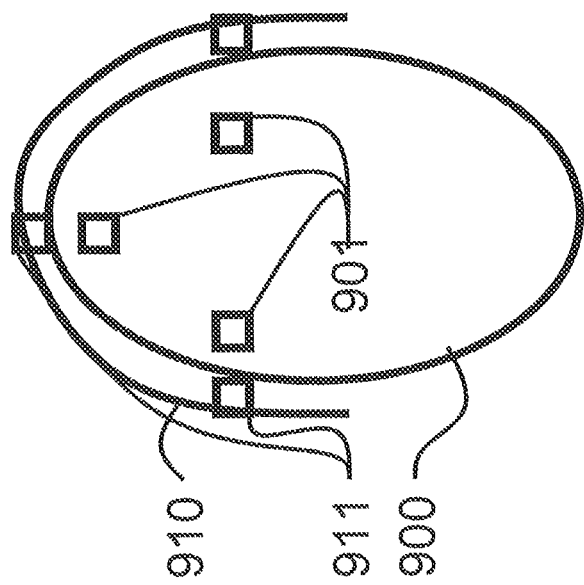
FIG. 9: ThinkingCap™

BRAINWAVE ACTUATED APPARATUS

CROSS-REFERENCE TO RELATED APPLICATION

This application is a continuation of U.S. patent application Ser. No. 15/392,483, filed on Dec. 28, 2016, which is a continuation of U.S. patent application Ser. No. 13/154,022, filed on Jun. 6, 2011, and claims benefit and priority from U.S. Provisional Patent Application No. 61/351,725, filed on Jun. 4, 2010, the contents of each of which are incorporated herein by reference.

BACKGROUND

The present invention relates generally to brainwave controlled devices, programs, interactive environments, and the like. Typically brainwaves are read using electrical contacts to the brain of one or more users. The electrical signals are amplified and supplied to a signal processing device.

SUMMARY OF THE INVENTION

In one aspect the present invention includes a brainwave actuated apparatus with a brainwave sensor for outputting a brainwave signal, an effector responsive to an input signal, and a controller operatively connected to an output of said brainwave sensor and a control input to said effector. The controller is adapted to determine characteristics of a brainwave signal output by said brainwave sensor and based on said characteristics, derive a control signal to output to said effector.

The brainwave sensor could be borne by the body of a user and the apparatus can have an environmental interface for interfacing to the environment of the user. The environmental interface can be coupled with the effector, correlated with the effector, or could itself be the effector. The effector could be an affective effector that expresses affect to other persons.

In another aspect, the invention provides a performance improving method, comprising: sensing a brainwave signal; determining characteristics of said brainwave signal; and vibrating a device with an intensity dependent upon said characteristics.

Various other embodiments and aspects of the invention are also disclosed.

In various embodiments, a brainwave actuated apparatus is part of an affective communications device, physical or virtual, or in mediated reality or cyborgspace.

In some embodiments I provide personal safety devices, personal data capture systems, medical devices, entrainment, physiotherapy with biofeedback, brain music concerts, training for the use of violin, cello, etc., using one or more electrodes in a multi electrode cap. For example, a skull cap with 16 electrodes is provided with a copper mesh that functions as a Faraday cage to shield the electrodes and also the mesh cap is the ground plane for an antenna that provides wireless communications, telemetry, and the like. A portion of the apparatus may be permanently attached to the body, in some embodiments, with detachable portions that provide additional functionality such as a seeing aid, where the Brain Computer Interface (BCI) portion of the apparatus may be permanently attached and certain extra task-specific features may be added as desired. For example, in a task-specific seeing aid, such as for certain specific seeing tasks (e.g. high contrast work such as electric arc welding) a specific kind of computer vision system can be plugged into a BCI cap. The BCI cap or "ThinkingCap"™ is designed to accept various plug-in modules such as for extra senses or extra effectors (as if, for example, extra body parts, of a sort). Additional "eyes", "ears", and the like can be plugged into the ThinkingCap™ as desired.

Some embodiments function as a seeing aid, and visual memory aid, or as a form of assistive technology. The invention can also function as a Personal Safety Device (PSD) like the "black box" flight recorder of an aircraft, but instead the invention provides a walk recorder, or personal capture device that captures EEG together with EVG (Electro Visuo Gram) for example.

Some embodiments may include a combination of brain electrodes, surface mount dry or wet electrodes, implanted or partially implanted electrodes, DermaPlants™, and the like, together with vibrotactile effectors. In some embodiments the electrodes are read-only and the vibrotactile effectors form the opposite pathway back to the brain. In this way, in some embodiments there is a complete Humanistic Intelligence feedback loop without the need to provide electrical stimulus to the brain, as some persons may find this uncomfortable. In some embodiments EEG is not needed at all. For example, a skull cap with vibrotactile effectors may read out of from a wearable computer fed by a 3d range camera such as a Kinect™ range camera, and write to vibrotactile effectors or electrodes or both. In another embodiment, the 3d range camera is responsive (by way of the wearable computer and BCI) to EEG signals in the feedback loop that adjusts the parameters of vision as then perceived by the vibrotactile effectors.

This apparatus therefore can provide vision to a blind person without the need to electrical stimulate the brain. It can do this by combination of occipital lobe readout to control 3d camera parameters that then images onto a vibrotactile effector array on the skull cap. The vibrotactile array moves with the head of the wearer, to spatialize the environment by allowing the wearer to scan the head side-to-side, or the like, and therefore, with a narrow Field of View (FoV) camera like the Kinect™, a blind person can find their way in a natural head-centric manner that mimics eye-based vision. The orbit of the whole head then replaces the orbit of the eyeball. With VideoOrbits™ image stabilization, the 3d environment can be scanned and understood in a wholistic way and spatialized as a natural direct-user-interface. This allows for a reality-user-interface (visual reality itself as a user-interface).

In some embodiments the system also works with SSVEPs (Steady State Visually Evoked Potentials), so, for example, a flashing light is shown to a user and the same waveform is read, via lock-in amplifier, or the like (monitored brainwave entrainment).

In some embodiments, eyeglasses such as EyeTap or virtual reality eyewear includes a headband to keep the glasses from falling off.

The headband goes behind the head to the occipital lobe, and may also work with dural electrodes, dermaplants, the ThinkingCap™, or the like.

The eyeglasses may also provide P300 (Positive, 300 milliseconds), and audiotory p300 with earphones.

Time-locked EEG signals known as event-related potentials (ERP) are useful in this context.

Wearable, implanted or dermaplanted systems are also possible in this context.

Dry readout through hair is also possible in a flexible eyeglass based display or the like, as well as in headworn apparatus.

A musical instrument like Spa Hero or Hot Tub Hero presents the player with colored lights and asks response on hydraulophone to get a score in a game.

Now it can also work by a person imagining what they're going to play, and the brainwave pickup of intention of what will be played or when.

In the future one may detect a person's intended actions from event-related potential (ERP), and with signal averaging of the Chirplet Transform, doing it 100 times or so, we can obtain useful information.

There is provided some sort of virtual on/off switch for the thought reading device, such as a thought reading camera that can be turned on and off when desired.

This works by going into a known sequence of brain states, such as state transition diagram from low Alpha low Beta to Beta high Alpha low, then Alpha high Beta Low then both high, or the like.

Also there is provided an adaptive system that changes the parameters of detection in accordance with changes in user condition, etc.

There is provided detection of intention state versus null state.

There is also provided sensory motor response: imagine moving your arm or foot, to get SMR (sensory motor response) data.

There is provided use of various ERPs such as visual N400 (negative 400 milliseconds), for use in a VMP (visual memory prosthetic), as well as with P2 (P200 i.e. positive 200 ms) which is involved in the memory processes, and visual N1.

The eyeglass safety band makes use of the fact that the Alpha waves are stronger on the occipital lobe.

The measurement of P300 is also occipitally, so that lie detection and the like can work with the thought reading camera of the invention.

Motor signals at top of head are read with a headband that supports the eyewear or the like, giving use of the sensory motor cortex.

There is also provided fabric electrodes for use with a hat, or the like.

Improvements to previous EEG work include detecting transitions and responding to transitions. Transitions are most notably signified by chirps (changes in frequency). This provides quicker response by detection of transitions. As compared with PLL, PLL is poor at low SNR. Chirplet Transform gives better performance at low SNR.

Alpha-Theta transition: Alpha waves bring about creativity, but so do Theta waves [Brain Activity by Terrance A. Bastian].

Much interesting activity rests at the transitions between these various states.

The Alpha Theta range arises in self-hypnosis, meditation, and religious teachings [Bastian].

Beta waves arise from focused concentration and mental calculations, or the like.

Drugs can be prescribed to help in meditation, e.g. to arrive at certain brain states, especially to help in problems of stress, but the drugs may have undesirable side effects, as well as a lasting aftereffect. Thus it may be desirable to control the state by methods such as biofeedback (i.e. closed-loop entrainment, and the like).

Whereas brainwave control may arise from comparison between Alpha and Beta, (i.e. between relaxation and concentration), for an inexperienced user, a more experienced user can independently control Alpha and Beta to some degree. For example, an experienced user may be able to elicit high degrees of Alpha and Beta activity simultaneously (i.e. high energy content in the 8-12 CPS range as well as in the 12-30 CPS range at the same time).

A system that trains a user, through, for example, biofeedback, may help train the user for such skills as may be desired in activities like archery or golf that require simultaneous concentration and relaxation.

Thus an apparatus of the invention may help people improve their abilities at such tasks by training with biofeedback.

In these various biofeedback means, a display means is provided in some embodiments. This may include a CRT or LCD or similar computer screen, but alternatively it is desirable that we can get into the relaxed state by closing the eyes. In this sense, an alternate form of biofeedback stimulus is one of hearing or feeling. Hearing biofeedback can be, for example, binaural tones for brainwave entrainment. In 1839 Heinrich Dove discovered that separate tones in each ear result in perception of beats.

Another form of feedback can be the sense of feeling. Many people soak in a hot tub to relax, or seat themselves in a comfortable chair.

The chair may be underwater (as in the fiberglass seat of a hot tub) or on land (as in a comfortable First Class airline seat in an inflight entertainment embodiment of the invention).

In one embodiment, there is provided one or more brainwave controlled pumps that pump fluid such as air or water against or near the user's body. The fluid may be heated and the temperature may be controlled by the brainwaves. Preferably there are a range of frequencies and effects at a plurality of pumps, such as one for the lower back and one for the upper back, or the like.

Isochronic tones may also be used with periodic pulse trains, quasi-periodic tone-bursts, or other energy bursts such as spread spectrum (e.g. periodic or somewhat quasi-periodic chirp bursts or the like).

Tactile and audiovisual entrainment, biofeedback, or the like is used to effect thalamic stimulation of the cerebral cortex, to affect cortical activity in a frequency range around 1 to 30 CPS over a large area of the body such as by tactuators, seating, hot tub jets, as well as audiovisual stimulus.

It is known that television has a sort of hypnotic effect on the watcher, thus causing different brain states to be reached. Similarly, a computer screen is directed in a more structured way, as part of a biofeedback loop, especially in the context of a relaxation tub or seat, such as an in-flight entertainment or relaxation application.

Another embodiment comprises a dream capture machine to capture dreams. The device is programmed to wake up the user from REM sleep which is the time when reams are most vivid, and then use non-movement of body to capture and re-enter. A Dream Editor is provided by way of using EEG to annotate the dream without movement of the body so that the user can re-enter the dream.

Alternatively, a Twiddler is used to enter dream text without movement of the body too much that the dream buffer is cleared so that the dream can be re-entered.

The Twiddler system uses the steps of:
(1) detecting when to awake the user;
(2) awakening the user then;
(3) accepting input text that describes the dream, said accepting not requiring appreciable movement of the body;
(4) entrainment to re-sleep the user.

BRIEF DESCRIPTION OF THE DRAWINGS

FIG. 1 is a schematic diagram of a mind-and-body embodiment,

FIG. 2 is a schematic diagram of a musical instrument embodiment,

FIG. 3 is a schematic block diagram of an in-flight entertainment embodiment,

FIG. 4 is a collection of graphs illustrating the Chirplet Transform in the context of the invention as it applies to tracking evolution of brain states, and the like, FIG. 5 is a side view of a violin bow made in accordance with an embodiment of the invention, FIG. 6a is a schematic diagram illustrating use of an embodiment of the invention applied to a toothbrush; in other embodiments, a dentist's drill, cleaning implement, massage implement, health aid, or the like may be substituted for a toothbrush, FIG. 6b schematically illustrates a multimotor embodiment of the toothbrush of FIG. 6a, FIG. 6c is a schematic diagram illustrating use of an embodiment in which an environmental interface is an antenna which is also the effector, by virtue of the fact that the antenna is also visible to others (e.g. it is anthropomorphised as tail), FIG. 6d is a schematic diagram of an acoustic embodiment, FIG. 6e is a schematic diagram a vehicular embodiment, FIG. 7 is a schematic diagram a hot tub embodiment, FIG. 8 is a schematic diagram a ThinkingCap™ embodiment, and FIG. 9 is a schematic diagram another ThinkingCap™ embodiment that has portions inside the head and outside the head of a user.

DETAILED DESCRIPTION

FIG. 1 is a diagram outlining an embodiment of the invention using a mind and body interface. A user 110 wears an electroencephalography device, EEG 120, with a wearable computer system, PROCESSOR 130.

The general idea of fitness to the mind and the body is of universal importance and has been well recognized throughout the ages. For example, the slogan that appears on most letterhead and official documents of the Massachusetts Institute of Technology is "Mans et Manus" which is Latin for "Mind and Hand", or more generally, mind and body. The basic idea is that we must understand theory at a deep level of the mind (mans) but also have the capacity to execute the theory through real world applications of the theoretical concepts, and take physical action (manus).

In training for this kind of real world symbiosis between mind and body, user 110 may be seated in a hot tub, or an airline chair for in-flight entertainment, relaxation, or training exercises, or the like, or in a spa or gym facility for entertainment, relaxation, exercise, or training.

The hot tub, seating, exercise equipment, or the like, may include an element for providing variable tactile stimulation. Such an element is sometimes referred to herein as a tactor. As used herein, a tactor is a type of transducer which converts an electrical signal to a variable tactile stimulation and which may also be capable of converting a tactile stimulation to an electrical signal. The tactor 140 in FIG. 1 is a vibratory chin-up bar which is the bottom rung of a ladder 145 which acts as a piece of exercise equipment.

FIG. 1 shows three points in time: leftmost is when the user first approaches the equipment and grabs the bottommost rung of the chinup ladder. At center is depicted when the user 110 begins to do a chinup. Rightmost is depicted when the user 110 does a chinup and a "mindup" at the same time (i.e. the user levitates himself or herself with his or her mind, while doing a chinup.

In this illustration, the tactor 140 is the chinup bar itself, which is, here illustrated, as the bottommost rung of ladder 145, along with a linear actuator that can raise the rung under computer programmed control by way of CONTROLLER 150. Controller 150 is a microcontroller or computer system equipped with interfaces. A satisfactory microcontroller is an Atmel ATMEGA48 microcontroller, and one of the six PWM (Pulse Width Modulation) outputs is operably connected to a linear actuator that moves the ladder rung up and down. A satisfactory linear actuator is a motor gear and cable system with steel cables inside both sides (left side and right side) of the frame of LADDER 145 made such as to raise one or more rungs of the ladder in response to an input to the processor. Input, such as from a spectral response in the range of 12 to 30 CPS (Cycles Per Second), corresponding to Beta waves from the brain of user 110, is collected from EEG 120 by processor 130, and transmitted wirelessly to controller 150. Analysis on processor 130, or controller 150, or a combination thereof, determines a state of concentration of user 110, such that the ladder rung of ladder 145 rises in proportion to the concentration factor of user 110. User 110 can raise this rung with the power of thought alone, i.e. simply by thinking in the right way, i.e. concentrating, such as to generate brainwave activity with a high degree of amplitude in the 12 to 30 CPS range.

User 110 can raise the chinup bar while doing chinups, i.e. experience a synergy of mind and body that allows his or her body to be raised up. This mind and body experience is not mere levitation with the mind, but, rather, a cooperation between his or her own mind and body that accomplishes a task that results in an exercise of both the mind and body at the same time, in unison, such as to train for such tasks as might require mind and body coordination.

Tactor 140 includes a tactuator (tactile actuator) which vibrates the tactor at a selectable frequency. This results in a tactile stimulus useful for brainwave entrainment. Preferably tactuator 160 vibrates in a repetition rate in the 1 to 30 CPS range. The actual frequency of vibration need not be in that range, but the repetition rate is preferably in that range. For example, a suitable tactuator for use in exercise equipment or hot tubs or seating, is the Clark Synthesis AQ339 geophone or hydrophone sometimes referred to as a "Aquasonic Underwater Speaker", although it is more of a geophonic or hydrophonic device than a loudspeaker (i.e. it is meant to move solid matter or liquid matter more so than to move air). In applications where the use is not underwater, but outdoors in light rain, an AW339 will suffice. Other gaming or home theatre transducers may be used, such as "butt thumpers" or "seat shakers" or the like.

The result is "tactile sound", i.e. a sensation of sound sent to the human body directly in solid matter, rather than through air.

As a result, a user in an airline seat can experience an effect without disturbing other people in nearby seats, because the acoustic impedance of solid matter is much different than air, thus resulting in large amounts of energy transfer being possible without much disturbance of the air.

In exercise equipment, the "tactile sound" can be felt without too much disturbance to other people using adjacent exercise equipment. In a hot tub, even a communal hot tub or spa, vibration of one individual's body can be achieved without too much disturbance to others, if desired.

It helps to classify transducers according to the state-of-matter in which they operate. I like to also enumerate them in the order of increasing thermal energy of the state-of-matter in which they operate, as follows:

1. solid ("Earth"): geophone;
2. liquid ("Water"): hydrophone;
3. gas ("Air"): loudspeaker or microphone;
4. plasma ("Fire"): ionophone.

These states-of-matter correspond (approximately) with the four Classical Elements (Earth, Water, Air, and Fire).

Since a tactuator is often a device that vibrates solid matter, it may either be a geophone or be thought of as being a geophone.

Referring back to FIG. 1, tactuator 160 vibrates the bar with tone bursts that occur at a rate of 1 to 30 tone bursts per second. Since many tactuators have problems delivering high energy below 20 or 30 CPS, each tone burst may be delivered at a frequency such as 200 CPS, to which the human sense of touch is very sensitive. This frequency range reduces energy requirements. Thus some relatively modest 200 CPS or 250 CPS pulses are delivered to stimulate the sense of touch, and this is done at a rate of 1 to 30 CPS, in order to do entrainment.

Brainwave entrainment is, in some sense, an inverse to thought-controlled technology. Thought controlled technology involves the use of the brain to control something. This might be called "telekinesis" or "psychokinesis" in which the mind directly influences a physical system.

The inverse is when a physical system directly influences the mind.

For example, during an exercise routine, let us suppose that user 110 is presented with a stimulus of around 8 CPS. Since this stimulus is in the frequency range of typical brainwave activity, one goal is to cause the brainwaves, at least in part, to lock onto that frequency of stimulus.

This form of brainwave entrainment works as follows: Controller 150 sends a signal to processor 130 which signal programs the processor 130 for receiving brainwave signals from EEG 120 and tuning to exactly same frequency as the excitation is presented, namely, in this example, 8 CPS. This is done by way of a lock-in amplifier, PLL (Phase Locked Loop), MuSIC (Multiple Signal Classifier), MFBLP (Modified Forward Backward Linear Predictor), or the like, so that there is determined a degree of correlation, or the like. Thus, with the user receiving a stimulus (say a vibration) at 8 CPS, the system can output an indication (as a biofeedback signal) of the energy in the user's brainwaves which are at 8 CPS.

More generally, brainwave entrainment need not be limited to sinusoidal signals of pure tone, but, may instead comprise spread spectrum excitation, or other arbitrary periodic or quasi-periodic signals that can be worked with the equivalent of a more generalized lock-in amplifier.

A standard lock-in amplifier such as a Stanford Research SR510 lock in amplifier can be used for sinusoidal signal detection. For example, we might excite the user at a particular frequency and then attempt to coherently detect the existence of that frequency in the subject's brainwaves. However, a better approach is to entrain desired brainwave activity more generally, with an arbitrary periodic excitation, and then measure, more generally, the response to this very excitation, with signal averaging, or the like.

Tactile and audiovisual entrainment, biofeedback, or the like, are constructed such that thalamic stimulation of the cerebral cortex affects cortical activity, in a frequency range around 1 to 30 CPS over a large area of the body such as by vibratory elements or other tactuators in seating, pulsating hot tub jets, as well as audiovisual stimulus.

Television can have a sort of hypnotic effect on the watcher, thus causing different brain states to be reached. Similarly, a computer screen is directed in a more structured way, as part of a biofeedback loop, especially in the context of a relaxation tub or seat, such as an inflight entertainment or relaxation application, or exercises for the mind and body.

Various forms of SSVEP (Steady State Visual Evoked Potentials are displayed on SSVEPTV 170 (Steady State Visual Evoked Potential TeleVision display). In this way, one or more senses can be stimulated for brainwave entrainment while part of an exercise or game or training or relaxation regimen is in process.

FIG. 2 is a diagram outlining an embodiment of the invention using multiple parallel or sequentially selected tactors, such as vibratory elements that can provide variable tactile stimulation. In FIG. 2, the tactors are rungs of a ladder 241, 242, 243, 244, etc., but in other embodiments they could also be handles of various golf clubs, tools, cleaning implements, or the like, or parts of a single object such as an airline seat and seat arms and chair back and tray, which form part of an in-flight entertainment system or in-flight exercise and relaxation system.

The bottom most rung of ladder 145, as depicted in FIG. 2, is fitted with a strain gauge resistance bridge, B0, as well as a geophone G0. The top of bridge B0 is supplied with a greater voltage, marked "+" and the bottom with a lesser voltage marked "−". The four terminals of each bridge are connected in reality but FIG. 2 only shows partial connection in a simplified form for ease of illustration.

The bridges are a matrixed in a 3 by 4 arrangement, to use 3 of the 6 analog inputs of the ATMEGA48. The bridges are supplied by voltage from output pins PB1, PB2, PB3, and PB4 of the ATMEGA 48, as referred to the Atmel ATMEGA 48 datasheet, or the pinout diagram, local cache of http://wearcam.org/ece385/avr/.

Were more tactors present, we simply use more pins, e.g. PB0-7 driving a 6 by 8 set of matrixed bridges into all six analog inputs provides 48 bridges.

The output of each of the 12 bridges (one for each rung of the ladder 145) is shown in FIG. 2 as being connected directly to pins PC0-PC2 (refer again to Atmel ATMEGA 48 datasheet for PC0, PC1, PC2, etc., pinout designators). This is merely for simplicity, because in actual fact we connect the two outputs of each bridge (i.e. left and right) to a differential instrument op amp (operational amplifier) and the output of that op amp is what is actually connected to the input pins PC0-2. Because of the matrixing, for the 12 rungs, we only require 3 op amps rather than 12 op amps.

The upper left and lower right resistors in each bridge are actually strain gauges on the bottom of the corresponding rung, so that stepping on the rung increases their resistance. The upper right and lower left resistors in each bridge are strain gauges on the top of the corresponding rung, so that stepping on the rung decreases their resistance (i.e. increases their conductivity, thus pulling the rightmost output voltage of the bridge more positive and the leftmost output of the bridge more negative, such that the differential op amp gives a higher output). Thus stepping on the rung with the foot, or pulling on the ring with the hand, causes a measurable output for each particular rung, that indicates flexion. Resistance bridges are in some ways analogous to a carbon microphone, and can "hear" sounds and other disturbances made in the rungs of the ladder, in addition to slow flexing. Thus the bridges pick up a frequency range that goes all the way down to 0 CPS, i.e. Direct Current (DC). In this sense, the sound spectrum that the bridges "hear" includes the origin, in frequency space.

In addition to flexion, we have one or more geophones on each rung that listen to vibrations in the rung. Geophones tend to pick up higher frequencies better, and they can also "listen" and "speak", i.e. they can create disturbances when fed with electric input. A suitable geophone is the previously mentioned Clark Synthesis AQ339 geophone or hydrophone. Alternatively, geophones G0, G1, G2, etc., may be piezoelectric devices.

HDR Proc. 250 (High Dymamic Range Processor) receives input from large-signal bridges B0, B1, etc., as well as small-signal listener geophones G0, G1, G2, etc., to obtain extended dynamic range over a broad band of disturbances and thus to sense both subtle and large flexion or sound or vibration in the rungs or whatever other input is used. The HDR Proc. 250 also outputs to various effectors such as also the rungs, or other objects that can be sensed or affected by user 110.

The rungs may be made of various materials such as metals, plastics, or wood. For simplicity, let us consider wood.

A xylophone is a well known musical instrument, and "xylo" is the Greek word for "wood" and "phone" is the Greek word for "sound". Thus "xylophone" is Greek for "wood sound", and thus the xylophone is an instrument made from wooden bars of varying length that are stuck by mallets. The word is sometimes used more generally to describe an apparatus consisting of other materials struck with mallets, although the term "glockenspiel" or "metallophone" is often used when the material is metal, and the term "lithophone" is used when the material is stone, etc.

Since we have an effector and a listener on each rung, we may establish a feedback loop that listens and an effector that actuates, such that when any rung is struck or touched by a user, it resonates at a desired pitch. Thus we can have each rung stand for any desired musical note, the sound being actually produced by the vibrating wood, such as to be an acoustic instrument, but with pitch defined by processing, such as a bandpass filter between listening and feedback to sending.

If we desire, for example, tactor 241, the bottommost rung of the ladder, is selected by one foot of user 110, and when flexed, is made to resonate or buzz or vibrate at 220 CPS which corresponds to an A note. The next rung is programmed to vibrate at 246.94 CPS, which corresponds a B note. The third rung is programmed to vibrate at 261.63 which corresponds to a C note, and so on.

In this way, the ladder of FIG. 2 is a xylophone, and it is played by striking, tapping, or flexing the 12 rungs of the ladder, each rung corresponding to the frequencies as follows:

note; freq/second
A=220.00
B=246.94
C=261.63
D=293.66
E=329.63
F=349.23
G=392.00
a=440.00
b=493.88
c=523.25
d=587.33
e=659.26

As an alternative to the bandpass filter algorithm just explained, we can also employ (instead of or in addition to, i.e. running concurrently) a frequency-shifting algorithm that maps the frequencies present to the desired frequency. Thus we shift from DC (0 CPS) up to whatever note is desired, e.g. bottom rung, shift from DC up to 220 CPS, etc. The frequency-shifter may be a simple ring modulator, pitch transposer, or frequency modulator, or frequency transposer. Frequency shifting is well known in the art, e.g. when singers are off key, and the pitch is corrected in post-production or in realtime during a live performance. Fourier spectral analysis, synthesis, waveshaping, and the like, as well as frequency modulation, and the like, are also well known in the art.

Thus we can make a wooden ladder in which each rung is the same length, but it behaves as if each rung were a differently length tuned to a different frequency. In this way, we have a xylophone with infinite sustain. As long as you stand on the bottom rung, you hear an A note sound and it never stops sounding until you take your weight off the bottom rung. When you stand on the third rung you hear middle C and if you put more weight on that rung the middle C sounds louder and if you put less weight on it the middle C sounds quieter.

The frequency range depicted here, i.e. 220 CPS to 660 CPS, is tactile, and in fact we may wish to drop the whole bank down an octave so it runs 110 CPS to 330 CPS, as that is centered nicely on the most easily human-perceptible range of frequencies.

The aforementioned "bank" is called a "filterbank" or "shifterbank" depending on which of the two algorithms are used. The first algorithm is called "filterbank" and the second is called "shifterbank", though the frequency shifter, if desired, may be thought of as a form of filter algorithm.

Thus, in this embodiment, the tactors are both sensors and effectors.

It should be understood that the ladder is just an example, for the tactor 241 can also be an airline seat, or the like, that provides tactile stimulation when sat on.

User 110, depicted in FIG. 2, wears EEG 120 apparatus. As he or she steps on rung 241, the oscillations in the rung may be made to depend on brain state. The oscillations in the rung may also be made to affect brain state, i.e. through entrainment, and the degree of this entrainment may be measured, and itself may be used to influence other activity in the system.

As depicted in FIG. 2, the user is flexing more than one rung at the same time, e.g. rung 241 and rung 249, which sounds and provides tactile feedback for two notes at once, i.e. low A and high B ("b"=493.88 CPS). More generally the user may flex one rung with each foot and one with each hand so we may tend to have 1, 2, 3, or 4 rungs in flexion at once.

The tactile action need not take place on a ladder, but could also occur on patio stones, walking, or on various parts of a seat, where a user could provide a tactile input signal by simply shifting weight from one side of a chair to another, or leaning back on the seat's upright portion, or reclining, or resting.

Referring back to FIG. 2, the capacity to programmatically affect the feedback space the user is in, i.e. "cyborgspace", means that we can assign dynamically varying meaning to each rung.

For example, the bottommost rung 241 can be made to play the first note of a song, rather than the first note of a scale. For example, let us consider the popular children's song "Chim Chim Cheree" from Mary Poppins. The first note of the song is a "C" and the second note is a "G". Here we have the first rung 241 thus play a "C" and the second rung 242 thus play a "G".

Climbing the ladder thus plays the song, either as notes, or perhaps sung, vocalized, by computer, as "Now as the Ladder of Life 'as been Strung . . . " for example. Thus the ladder becomes an andantephone (http://wearcam.orgiandantephone/).

The user can move through the song with the body, the mind, or a combination of mind and body, by using entrainment, or thought controlled technology, to select or be affected by the various frequencies on the Ladder as shown.

Every third rung could play a whole chord instead of just a note as follows, for example, first rung 241 is for a C minor chord: the processor selects three passbands, 261.63 CPS, 311.13 CPS, and 392 CPS. These are fed back adaptively to make the third rung resonate simultaneously at all three frequencies.

The same thing can happen while seated. For example, tapping on the arm of a chair, we can get it to resonate at three frequencies at once, to form a C minor chord, by having geophones such as geophone G0 listen to the tapping, process that information with a bandpass filter or frequency shifter, or combination thereof, and then output to earphones, or, alternatively, output to the other arm of the chair, or that very same chair arm that is the input device, or to a combination of the tapped arm and the rest of the chair.

Moreover, various apparatus can be fitted into a seat of a passenger craft to create an interactive experience attractive to first-class passengers who might be provided this experience free of charge as part of a promotion to upgrade to first class, or might be provided to coach class passengers for a small additional fee.

FIG. 3 is a diagram outlining an in-flight entertainment embodiment. This illustration is shown from the top, i.e. looking down from the ceiling of an airplane or train or bus or yacht or cruise liner or boat, or car, or private jet, or other vehicle or home theatre, or hot tub, pool, spa, or the like, at four seats. Whereas reference is made here to in-flight entertainment, it should be understood that this setup applies to other settings such as a spa, where users are seated at various stations, such as might occur in a place like SpaWorld USA in Washington where there are various stations for users to soak and relax in, such as rows of adjacent seating areas, or also disparate seating areas. The seats here shown are adjacent, but, by way of networked communications, may be spread throughout the world, e.g. a user of a station in SpaWorld USA might commune with someone on an airline, in-flight, by way of wireless networked communications between these different venues. People on cruise ships, yachts, and airlines, and people in hot tubs might all share in a common collective cyborgspace in a communal experience.

A first user 311 is seated on a chair or airline seat having a left armrest with a tactor 341 and a right armrest with a tactor 341R. User 311 can tap on one of the armrests, such as monitored and affected by tactor 341. The tactor can vibrate itself but also, each time the tactor is struck or tapped or rubbed by the user's hand, for example, it can cause various events. For example, tapping the tactor 341 can sequence through a song, such as an andatephonic song like "Chim Chim Cheree" (Mary Poppins), or "Perpetual Motion" (Suzuki), or any other song that can be suitably andantephonized, as described in the ACM article: "The andantephone: a musical instrument that you play by simply walking", by S. Mann, which appeared in ACM Multimedia 2006, pp 181-184.

Let us consider the user 311 tapping the arm rest, which gives the notes or harmelody (harmony and melody) according as follows:

Tap 1="Now" (loud)
Tap 2="as" (quiet)
Tap 3="the" (quiet)
Tap 4="Lad-" (loud)
Tap 5="-der" (quiet)
Tap 6="of" (quiet)
Tap 7="Life" (loud)
Tap 8="'as" or "has" (quiet)
Tap 9="been" (quiet)
Tap 10="Strung" (loud) where every third tap is emphasized because this song is in triple time (i.e. "3/4 time" if the unit of each tap is a quarter note).

Songs in quadruple time (i.e. "4/4 time" if the unit of each tap is a quarter note) can be programmed in which case every fourth tap is emphasized, etc. Alternatively other ambient or meditative environments are programmed for relaxation, mediation, exercise, or training. In addition to tactor 341 there is also a "butt shaker" 342 and a "back shaker" 343. Shakers 342 and 343 respond to controller 350 which receives input from (as well as gives output to) tactors 341 and 341R.

Shaker 343 is in chair back 345 and vibrates the vertebrae of the user 311 to perform a backrub, massage, or tactile effect of sorts, or is simply to interact and communicate with the user or entrain the user 311.

One or more users may play together, e.g. two users can "jam" on the same song, simply by tapping their fingers to generate the song.

This is not merely tapping to the beat of a song, but, rather, the tapping actually controls the volume of the sound through a frequency shifting schedule, i.e. a song matrix, that is loaded or reloaded for each phrase of the song, and each song.

For example, suppose users 311 and 312 decide on a song like "Chim Chim Cheree". Once they agree on a song, the frequency shifting matrix is loaded, and they can tap out the song to generate it. The controller 350, which is a computer or microcontroller, or the like, listens to input from tactors.

The first strike or tap is detected, and the processor selects three passbands, 261.63 CPS, 311.13 CPS, and 392 CPS, from the first entry of the song matrix. Each column of the matrix is a point in time, and each row is a note. Thus a column is a list of frequencies, and each tap or strike moves to the next column. In the second column we have only one frequency 392.00 CPS, and so on, such as to generate chord, note, note, chord, and so on.

The tapping gets the body in motion, and as with drum beats, it is well known that meditation and entrainment result. See for example, "Drums not Drugs" by Mikenas, Edward E. Percussive Notes. April 1999.

This drum therapy is combined with biofeedback, through SSVEPTV 370. SSVEPTV 370 also displays musical material of the song, as well as calming material such as scenery that moves with the music or rhythm through various phases, such as visual imagery that moves through the four seasons while user 311 taps out the music of Vivaldi's "Four Seasons".

Movement, rhythm, relaxation, and exercise and activity are all combined in the seating.

Additionally, the scenery is displayed with the correct horizon line as determined by accelerometer, inclinometer, and sensor 370A or from the airline's own instruments as received by controller 350 which then knows which way the plane or boat or car or the like is angled. In this way, the apparatus alleviates motion sickness because the displayed material is properly oriented with a synthetic horizon line that matches.

Thus if we see a winter scene, or summer scene, the horizon in either case matches reality, so that the visual and vestibular cues are matched between cyborgspace and reality even though users 311 and 312 are in some alternate cyborgspace.

Multi-player games are also possible. In another embodiment, users 311 and 312 view SSVEPTVs 370 and 371 where they view content. The content need not necessarily be limited to VEPs (Visual Evoked Potentials).

For example, two players may view a task on screen, and their brain states may be additive, so that they must cooperate in getting their minds in a similar state to complete a goal. For example, we may have a collective mediation in which both players must mediate into high alpha (relaxation) state, and something is displayed as the sum of the alpha waves of all players. This challenges the idea of one player against another, and instead results in collaboration, and trains people to collaborate.

FIG. 4 is a diagram showing signal processing and display of brainwave data. At the top of FIG. 4 is shown the Chirplet Transform of the brainwave data, segmented into meaningful quantities. The Chirplet Transform was invented in the 1980s and first published in the following reference: S. Mann and S. Haykin, "The Chirplet transform: A generalization of Gabor's logon transform", Proc. Vision Interface 1991, 205-212 (3-7 Jun. 1991).

An adaptive neural network for processing time-varying frequencies was also presented in 1991: S. Mann and S. Haykin, "The adaptive chirplet: An adaptive wavelet like transform", Proc. SPIE 36th Intl. Symp. Optical and Optoelectronic Appl. Sci. Eng. (21-26 Jul. 1991).

The axes of the Chirplet Transform are commonly taken to be beginning frequency 450, Fbeg/S, as shown on axis 410 and ending frequency 460, Fend/S as shown on axis 411. These are denoted quantimetrically, i.e. as dimensionless quantities that range from 0 to 30 CPS, where the per seconds is incorporated into the axis label to make the quantities along the axis itself dimensionless, i.e. 0, 4, 8, 12, etc., on an axis that is, itself, inverse seconds.

The chirplet transform is displayed as a greyscale or color image, in two dimensions, with color or light quantity denoting intensity. For example, high intensities may be denoted in a bright color like red. A red blob near the origin 400 denotes brain death, i.e. zero frequency, and hopefully that is not the dominant frequency component. Note of course that there will be some components at various frequencies, so we won't have merely one single point, but, rather, various points in this two dimensional image plane that may be displayed on SSVEPTV 370 or the like, during diagnostics, training, or the like.

Alternatively some further transformation may be done, i.e. images corresponding to chirplet transform states may be used to elicit other states.

States are denoted, such as state 420 in which the user is asleep at the beginning and ending of the analysis period. State 430 indicates the user has just awoken. Thus when the user awakes, we expect to find a strong chirplet transform component in this region because the brainwaves went from a theta component being strong at the beginning to an alpha component being strong at the end.

State 422 indicates an Alpha to Alpha transition, i.e. a predominance of remaining in Alpha, i.e. an unchanging relaxation.

State 470 indicates an entry into sleep state (transition from Alpha to Theta range).

The heavily drawn axes 411 and 412 are of great importance because they denote the boundary between Alpha and Beta states, i.e. between relaxation and concentration.

Region 480 denotes a downchirp region in which brainwaves transition from Beta to Alpha and thus this region denotes a region in which concentration is decreasing.

Region 440 denotes an upchirp region in which brainwaves transition from Alpha to Beta and thus this region denotes a region in which concentration is increasing.

Region 490 denotes a steady-state concentration in which concentration is unwavering.

Thus we can see that the Chirplet Transform is a suitable detector of various brainwave states, and, especially a detector of brainwave state transitions.

At the bottom of FIG. 4 is a state transition diagram indicating 4 states: state S1 (weak brainwave activity), state S2, strong brainwave activity in the Alpha region for 8 to 12 CPS, state S3, strong brainwave activity in the Beta region from 12 CPS and up, and state S4, strong brainwave activity in both Alpha and Beta.

Many tasks, games, and activities such as shooting (e.g. police snipers and anti-terrorist task force work), archery, music (e.g. violin and cello performance holding a bow), golf (e.g. a steady hand on the club), and sailing (e.g. a steady hand on the tiller) require a combination of high concentration and high relaxation.

This may seem counter-intuitive but the high concentration alone will not work for playing violin or the like, because there is a need to have both regions of the brain's spectrum (Alpha and Beta) working together.

For this purpose, an upside-down spectrum display 401 may also be helpful, as it has a unique physical interpretation in which higher values of the spectrum denote deeper thought, i.e. as we go deeper into concentrating and thinking deeply, spectrum plot 404 is indicated, i.e. deep in Beta. Deep concentration gives a spectrum like that shown in plot 405, which is deep in Alpha (i.e. high in Alpha wave energy, i.e. high in spectral energy between 4 CPS and 8 CPS).

Using such an upside down spectral display helps people train themselves to think deeply and broadly.

The goal, is to "will" through conscious thought and effort, the spectrum to take on a shape like that of plot 406. By concentrating on the plot, the user tries to deepen AND broaden their thinking, to span a broad range of brainwave activities as deep in thought (i.e. as high in amplitude) as possible.

This corresponds to state S4 in FIG. 4, where Alpha and Beta waves are both strong.

These raw displays are useful but to make the system more fun to operate, we can also use, instead, visual imagery and other interpretations of the chirplet transform, Fourier transform, wavelet transform, and the like, in various ways as part of a biofeedback-based in-flight entertainment system, or the like.

Additionally, in a preferred embodiment, a neural network is used to classify and auto-calibrate to changing conditions, especially in ambulatory (e.g. wearable computing and cyborg technology) applications. This may be accomplished as follows:

Capture brainwaves over a sliding window;

Apply LEM (Logon Expectation Maximization);

Classify the space spanned by a particular user in a particular circumstance (e.g. a particular business executive in a particular seat of a particular aircraft, or the like);

Auto-calibrate to this spanned space;

Initiate biofeedback in the form of a game or training scenario such as yachting, archery or golf that might appeal to the demographic of the user;

Re-adjust logons in the Chirplet Transform to classify brain state;

Provide a visual "reward" for success, e.g. a graphical depiction of a high score or success, when there is a high transition fromAlpha to Beta as depicted in State 430, or an even higher score for being in State S4 where both Alpha and Beta are high at the same time.

Other classification schemes can also be used, such as by grouping chirplet, spectral, frequency, sequence, etc., information for adapting to an individual user, classification, and the like. For example, spectral energy and brain states can result in features distributed in a two-dimensional or higher space of $F_{beg}$ versus $F_{end}$, or Alpha versus Beta, or the like, and clusters of data can be grouped by algorithms such as some number "K" of closest neighbors ("KNN") or by weighted K Nearest Neighbors, (WKNN), and the like.

To the extent that the data is often scattered anisotropically, a Singular Value Decomposition (SVD) is performed, or the data may be re-adjusted by way of a Choleski Factorization. Equivalently, PCA (Principal Components Algorithm) is applied.

Thus the user may be presented with a space having one or more dimensions, such as an image (two dimensions) on the SSVEPTV 370, so as to be able to guide a cursor or other object on the screen using thought alone, and to achieve meditation, relaxation, or various exercises in combination with other people, and with various tactors and other devices in, on, or around the seating or space.

FIG. 5 is a diagram showing an embodiment of the invention built into a violin bow. The physics of a violin are well known. See for example, an article entitled "Why is the violin so hard to play?" by J. Woodhouse and P. M. Galluzzo Plus Magazine Living Mathematics, Issue 31, http://plus.maths.org/issue31/features/woodhouse/index.html.

Here is a brief quote excerpt from the article:

When you pluck a note on a guitar string, there isn't very much that can go wrong. You may not play the right note at the right time, of course, but a single note will always come out at the expected pitch, and sounding reasonably musical. When a beginner tries to play a violin, things are much more difficult. When a bow is drawn across a string, the result might be a musical note at the desired pitch, but on the other hand it might be an undesirable whistle, screech or graunch. This difference stems from a fundamental distinction between the physics of plucked and bowed strings.

See also, Fiddler—bowing gestures From: schoondw Apr. 12, 2009, http://www.youtube.com/user/schoondw. One important thing that makes a good violinist is an ability to focus and relax at the same time. Accordingly, a violin bow 500, archery bow, musical bow, golf club, toothbrush, ski pole, or other implement, such as bow 500 (but not limited to a bow), is fitted with various brain interfaces, such as servo 501 that adjust parameters of the implement.

This invention may be applied to various devices like toothbrushes, dentist's drills, polishing devices, floor polishers, massage devices, electric drills, and reciprocating saws like a Sawzall™ (electric hacksaw often used for demolition).

In the case of a toothbrush, servo 501 may simply be a motor that runs the bristles, in rotary or reciprocating fashion. In the case of a Sawzall™, servo 501 is the main motor that powers the Sawzall™.

In the case of a violin bow, servo 501 turns screw 502 to adjust the tension on horse hair 510. This allows the player to continuously adjust the tension of the bow under program control. The hair 510 runs from the top end of bow 500 down to the frog 540, which houses a microcontroller, such as an Atmel ATMEGA AVR. This controller 550 receives input from a receiver that receives brainwaves from user 110 or 310, and there is provided a detection or estimation of Alpha and Beta activity of the brainwaves. The brainwaves or control from the brainwaves are received by antenna 570.

Most violin bows have a coil of wire around near the pad, to help with grip, and this coil 560 doubles as an inductive loading coil for the antenna 570.

An algorithm and system is used to vibrate the bow to notify the user 110 that he or she is not in the "zone" for optimal performance. This algorithm and system is as follows: Upon detecting shallow thought, such as a lack of simultaneously high Alpha and Beta activity, a vibrator 541 is activated by processor computer algorithm in controller 550.

This vibration can be felt in frog 540 and pad 530 as well as anywhere on the bow.

Using biofeedback, the user concentrates on quieting the buzzing or vibrating of the bow, and this has a simultaneous calming and alerting affect.

Thus the player is able to stay calm and focused at the same time, by using biofeedback to "will" the bow to "calm" itself.

The handle of whatever implement is being used may also have some kind of user-interface that can be perceived by the user.

Here it is useful for me to introduce the concept of a transmitient user-interface and a recipient user-interface, in situations where there are two or more persons involved.

In the example of the violin user, the violin user is the transmitient and members of an audience are recipients. In an embodiment of the invention one or more recipients may wear an affective computer of sorts that reads their sense of the experience. For example, recipients might wear something that reads their EEG signals and determines if they are annoyed or pleased or the like. When one or more audience members are annoyed, the violin bow may give a small electrical "jolt" to the player, not strong enough to cause pain or skin burns, but just a little "tingle" to indicate how the audience is feeling. The thing that gives the player the "jolt" is something I call a "transmitient interface". By "transmitient interface" I mean a user-interface intended for the transmitient.

In the example of the dentist, the recipient is the patient and the transmitient is the dentist. A transmitient user-interface, in one aspect of the invention, is a handle on the dentist's drill that heats up when the patient is feeling pain as read by EEG electrodes, EMG electrodes, etc. worn by the patient. The transmitient user-interface works as follows:

1. A recipient is fitted with pain sensors embodied as electrodes feeding into a signal processors. Alternatively or additionally, there are strain gages in the arms of the dental chair that sense hand clenching. A simple machine learning algorithm may aggregate these two or more signals using a support vector machine or other simple classifier or pain signal analyzer;
2. The pain sensors transmit a pain indication signal to a TUI (Transmitient User Interface) device, such as the handle of the dentist's drill. The handle may then emit an audiovisual feedback signal to the dentist, or it may heat up, or cool down, in response to varying degrees of pain, or the like.

In the latter case (e.g. when the TUI signal is a heating up or cooling down) the TUI may be said to be or include an "energy modulator". The energy modulator is a source or sink of energy that can be felt by the dentist. In the case of a heating or cooling that energy is thermal energy. In this way the dentist (transmitient) can feel the pain caused to the patient (recipient).

The result is a system that mimics how real life works. For example, when I drill a number of holes into a concrete wall, I can feel the drill heat up after a while. People sometimes even personify the drill, as saying "she's overheating". Thus if the drill is being overworked, I can feel "her" pain.

Thus the dentist can feel the patient's temper or patience "heat up". Therefore when my dentist feels the heat in the TUI handle build up, he would know when to "back off" a little.

Moreover, in another aspect of the invention, in which electroanalgesia such as transcutaneous electrical nerve stimulation (TENS) is being used, the electrodes that are being used to stimulate the patient may also be used to sense the patient's degree of pain. In this way the patient electrodes can even be both a TUI and an RUI (Recipient User Interface).

FIG. 6a is a diagram showing a toothbrush embodiment of the invention.

More generally, within the scope of the invention, a body-borne implement or apparatus may be hand-held, worn on the body, implanted partially on or in the body (as for example a medical device), or partially implanted and partially worn, partially handheld, or the like.

In a toothbrush embodiment the implement may be handheld.

Toothbrush 600 has a motor 610 which is a drive that rotates or reciprocates brush 621 in response to processor 650. Processor 650 is responsive to brainwaves of a user 110 of the brush or to brainwaves of a second user 611 receiving input from the brush.

Here is a situation depicted in FIG. 6 of parent and child, in which the parent and child are both wearing brainwave sensors and the parent and child both feel the action of the toothbrush.

A game is set forth in which both participants, i.e. user 110 and user 611 get into the same brainstate to drive the brush. Making the act of brushing teeth into a game will encourage it to happen more often and more willingly by all participants. Additionally the game can have state-variables that are saved, so that it might encourage people to brush more often and keep track of brushing. This peer pressure may also help. For example, if a person forgets to brush, they can be represented as an avatar of a goat, or a rat, to symbolize that their mouth stinks like a goat or a rat. A rodent breath symbol may thus appear in their online avatar of an online tooth brushing game. This may help use online peer pressure to encourage tooth brushing.

Additionally an oral camera 620 allows parent and child to see cavities and provides an educational element to the brushing experience, as well as captures images that can be sent to or brought to a dentist or oral hygienist for question and answer meetings, or the like.

A tactor 640 adds to what is felt in addition to sensations resulting from the motion of the brush due to the action of motor 610, thus allowing the tactility to be multidimensional. Tactor 640 can, for example, be a geophone that provides sound that is perceived due to bone condition through the teeth. The tactor 640 may play music in the same key as motor 610 so that a nice harmony results that can be felt. The song may also last a duration of a proper tooth brushing cycle. Accelerometers in the toothbrush handle also may feedback into this process. For example, music can be synthesized that matches the beat or rhythm detected in the brushing. Thus the music follows the rhythm of the brushing. The motor is modulated to capture the root note of the chord being played in the music at a particular time and the tactor 640 plays along with this music. Tactor 640 can also sense as well as effect, e.g. in some embodiments tactor 640 may "listen" to the tooth brushing sounds and determine a rhythm as a form of user-input to the process.

A bridge 640B measures flexion and gives feedback. One example feedback algorithm is such that the parent user 110 can feel the degree of action of the brush in the child's mouth. To do this, bridge 640B as read by processor 650 indicates action, and action is computed and fed to tactor 640 which the parent can feel. This action may clock the music along, or otherwise affect a gaming situation or online experience.

Additionally, stall forces on motor 610 are computed and this additional information is fed to a combined action algorithm that is affected by the child's brainwave activity that the parent can feel, so that there is a mutual awareness of painstate and brainstate to sense action, and affect.

More generally, an implement may have both a TUI (Transmitient User interface) and RUI (Recipient User Interface). For example, the handle of the toothbrush may be or may include the TUI, and the head ("business end") of the toothbrush may be or include the RUI. Like the dentist's drill, the handle of the toothbrush could heat up when the child's temper is "heating up" (as sensed by the head of the toothbrush or by additional apparatus such as EEG headband or the like).

Moreover, the transmitient-recipient pathway need not be hierarchical. For example, both ends of the toothbrush could have affectors (affective effectors), so that each person can feel (e.g. by heat) what the other is feeling (mood or temper or the like). This embodiment can extend to groups of people. For example, a group of workers can be drilling through a concrete sidewalk and each worker can "feel" the mood of their fellow workers. Additionally they might feel the "pain" of the road itself if they were to drill too close to a natural gas line, for example. Each drill is equipped with a TUI so that the workers can feel the results of their collective action as portrayed on this feedback path.

More generally, the recipient need not be physically a person physically present, and may, for example, be a representation of another person at another location, or may be a computer system of sorts, as might thus embody the concept of Humanistic Intelligence as defined in the book, "Intelligent Image Processing" (Author=Steve Mann, published by John Wiley and Sons, Nov. 2, 2001, 384 pages).

In any of these devices, there may be multiple effectors, multiple tactors, multiple motors, or the like. Even one individual TUI or RUI may contain multi-dimensional motors, tactors, effectors, affectors, or the like.

In the head of the toothbrush, for example, 2 motors can create complex patterns due to compound motion. When the motors run at rotational rates in the ratio of small whole numbers, the sound made by the device is musical in nature, and the patterns can mimic simple parametric curves, similar in some ways to the Lissajous figures, seen on an oscilloscope that plots one input against another input, each being a sinusoidal waveform in the frequency ratio of small whole numbers.

Feeding different spectral bands of EEG into each of just 2 motors can create a widely varying compound motion that can remain quite interesting (much less monotonous) for long periods of time.

FIG. 6b depicts a system with two motors, motor 610 and "Motor2", depicted as motor 612. A battery pack or battery box 601B is for receiving customer-supplied cells 601C such as type LR6 (GD) 1.5 volt AA cells. In a simple embodiment, depicted here is a four-cell compartment that may be filled with any number of one or more cells. If a plurality of cells are inserted they may be connected in parallel and supply a DC to DC converter with 1.5 volts that gets converted to a desired or possibly regulated operating voltage. Alternatively, it is preferable to have a switching network, comprising a solid state switch 600SW. The switch 600SW can be a form of crossbar switch that receives input from any number from one to four cells, inserted having any polarity (e.g. it does not matter which way the cells are inserted) and the crossbar switch automatically senses the number of cells and their orientation and connects them in series.

In this example, three cells have been inserted with the same orientation (all of the positive caps upward) and are automatically connected in series to provide approximately 4.5 volts to DC to DC converter 600DCDC.

The DC to DC converter 600DCDC supplies five volts, regulated, to a processor 600P which controls two "H" bridges, one for each motor 610 and 612. For simplicity of the drawing, only the connections to motor 610 are shown. The connections from "H" bridge 600H to motor 610 are depicted as connections 610HC.

Processor 600P drives motors 610 and 612 and can be used thusly to synthesize various musical effects. For example, motors 610 and 612 can rotate at different rates to create a superposition of musical sounds in the tooth brushing. Let us consider, for example, that the tactor 640 is playing a simple melody like "Twinkle Twinkle Little Star" that goes something like "CCGGaaG", "rest", "FFEEDDC", and so on. We might wish motors 610 and 612 to synthesize a nice harmony like chords "C", then "C", then "F", then "C", for example. This might be done by having motor 610 produce a "C" and motor 612 produce an "E" initially then an "E" again, then an "F", and then an "E" again, for example. The motor 610 is driven by the processor 600P to rotate at, or otherwise produce, a certain rate of rotation or vibration consistent with the number of cycles per second present in a "C" note, or low "C" note which the user perceives as sound.

Low cost motors often do not reliably rotate at a known rate of rotation without expensive feedback control devices. While we may have a shaft encoder or Hall effect sensor, or the like, within the scope of the invention, feeding back to processor 600P, we prefer, instead, to use the motor itself as the sensor. Motor sense signals 600M1S are picked up from the motor back to processor 600P as balanced differential inputs. Processor 600P senses the voltage spikes across the motor. In the case of a brush based motor these voltage spikes are considerable and are easily sensed. Alternatively, or additionally, a current sense signal 600CL is sensed as a current loop from a wire wrapped around one of the motor leads back to a differential balanced input to processor 600P.

Once processor 600P can sense the motor's electrical properties (e.g. noise made by the motor or periodic changes in the motor's current consumption, or periodic voltage spikes, or the like), it can then enter into a feedback loop to maintain a desired rate of rotation or vibration, and thus a desired musical note or tone pitch sensation.

With a plurality of motors, various musical, audio, and tactile effects can be created. Such effects include vibrato (chirping) or tremelo. For example, if motor 610 produces a somewhat periodic signal that can be approximated by a signal $S\_1$ at its fundamental frequency or pitch period, as $S\_1=\cos(2\pi\ f\_1\ t)$, and the other motor 612 produces a signal approximated by fundamental signal $S\_2=\cos(2\pi\ f\_2\ t)$, then what the user may hear or sense or feel or otherwise perceive may be something of the form $S=S\_1+S\_2$.

Since $S=2\cos(2\pi\ f\_d/2\ t)\sin(2\pi\ f\_s/2\ t)$, where $f\_d$ is the difference frequency $f\_1-f\_2$ and $f\_s$ is the sum frequency $f\_1+f\_2$. In certain frequency ranges, e.g. typically less than 20 cps (Cycles Per Second) the human perception system will perceive this signal as a tremelo, e.g. as an amplitude modulation envelope signal having a beat frequency of $f\_1-f\_2$.

Thus what is felt or heard or sensed can be much lower in frequency than either $f\_1$ or $f\_2$. This allows for the creation of subsonic percepts.

More generally, the apparatus can therefore create subsonic sensory stimulation from higher pitches (and therefore greater forces from smaller and lower cost motors) than might otherwise be possible.

Since brainwaves, and in fact much of human tactile sensation, occur at subsonic frequencies, there can be strong subsonic stimulation that is matched to the human physiology in various ways.

It is known that human feeling is very effective around 200 cps, or so, e.g. devices like the Tactaid™ make use of these frequencies. Therefore, in one aspect of the invention disclosed herein, we may wish to have tactors that operate at optimal tactile frequencies around 200 cps yet create tactile percepts at much lower frequencies as set forth by the difference frequency $f\_d$. This may be done by using a plurality (e.g. two) of tactors that are co-located. Two co-located motors, or two vibrators, for example, can therefore provide slowly undulating periodic stimulus that may gently massage gums or the like.

The apparatus is enclosed in a waterproof environmentally protected enclosure or housing 600W.

This invention is not limited to a toothbrush, and in fact may be used in any context where users control a vibrating or vibrotactile implement that they or each other or others can feel. Multiple users can use their brainwaves to control a local implement or a remote implement or both, allowing a sense of touch to transcend geographical boundaries.

This invention can also take the form of various robotic apparatus that is either worn or handheld, and can be vibrotactile or simply visual (decorative fashion, for example). Consider, for example, a Halloween costume that has a robotic tail. The tail may "wag" or jyrate due to effectors running from brainwaves. In this sense the tail creates an emotional or affective display. A person can then wag his or her own tail by thoughts alone. Additionally, a person can invite others to wag his or her tail by their brainwaves, through wireless link. With multiple frequencies present, the tail waves around in various forms not necessarily limited to simple Lissajous figures, but also more complex patterns owing to the mechanical resonances that are possible. Fitting the tail with mass-spring apparatus of sorts, it can function like an iambic (biambic) keyer and swing around in various ways that are partial to a biofeedback loop shared by the wearer and one or more others.

Humans can therefore, like dogs, express their affective (emotional) states and various appendages and robotic indicators (perhaps even light sources, illumination patterns, in addition to servos and the like) can be provided. We know, for example, when not to bother a dog. Like the way that a snake will hiss when not wishing to be disturbed, we can read a dog's internal state through the tail. This is one of the reasons dog owners sometimes cut off the dog's tail, so that the dog will look meaner or at least be hard to "read" emotionally.

In this way the apparatus of the invention forms a visual robotic emoticon of sorts.

A mechanical robotic tail can also take on a functional as well as affective aesthetic form.

For example, the functional form of the mechanical tail might be that of a communications antenna. The resulting Antail™ product (antenna tail product) stands up to attain better wireless communications whenever a better network connection is required.

This provides multifunctionality, e.g. the Antail is both a functional network connection as well as a visible indicator to others that a network connection bandwidth is increasing.

An attacker, rapist, or robber stalking a victim might, for example, see the victim's Antail™ stand up. This action, combined with a direct gaze of the victim, might serve as a deterrent.

It is often said that a victim should "Make eye contact if you are being followed by someone who you think is a potential threat. An attacker may be less likely to strike if they think you will be able to clearly identify them.", WikiHow, "How to Prevent a Potential Rape", http://www.wikihow.com/Prevent-a-Potential-Rape But a murderer may have less such worry because by killing the victim they have removed the possibility of being identified. Thus an attacker may perpetrate rape and murder or robbery and murder in order to not be identified.

But if the victim is using the apparatus of the invention, one or more video cameras combined with a very obvious network connection may provide a degree of deterrence. In this way the perpetrator can see that he has been seen by one or more cameras and that he has aroused a network connection bandwidth increase.

While many perpetrators may not be consciously aware of all of these things, they can see that there is some kind of apparatus that is responsive or appears "alive" in some way, and this in itself may serve as a deterrent in much the same way that a cobra puffs up its head when it feels it may become the victim of an attack.

In operation this aspect of the invention may use a brainwave sensor on the occipital lobe that reads visual brain activity, or it may also read off ECG (heart rate) and motion vibration sensors or the like.

When a victim is attacked and shaken the antenna goes up more. When a victim's heart rate goes up, apart from exertion, the antenna goes up. For example, the antenna can go up in response to a saliency index, such as heart rate divided by footstep rate. When an attacker pulls a gun on a victim, their heart may skip a beat but ultimately, on average, it will tend to go up over a short time interval, while the footsteps stop or slow down at the request of the attacker. If a person suddenly "freezes" while their heart rate escalates, it might be that they are being attacked, and the antenna may thus rise to full transmit capacity.

In some embodiments the antenna or associated personal safety apparatus may be combined with other deterrents such as pepper spray that discharges when or if the apparatus is grabbed. Alternatively the antenna itself may transmit a strong signal in an emergency and this may be enough to cause RF (Radio Frequency) burns on the hand of an attacker who tries to grab it.

The Internet connection will always work, generally, but it will rise to maximal capacity when it is "aroused". Thus the Internet itself may be regarded as a peripheral part of the body that rises and falls in response to the mind and body of the person upon which it is borne.

In addition to the prevention or deterrence of physical attacks, the invention may also be used in a fun and playful way. For example, the video cameras and transmitting antenna or network connection antenna can form a visual indicator of some otherwise invisible mental brain state. Such a device might take the form of a CAM™ (Cortical Activity Monitor) or MICA™ (Mechanical Indicator of Corital Activity) that displays brain activity in a fun and playful way.

Other examples of visual indicators can include robotic whiskers, robotic snake scales on a shirt or other garment, or robotic hair pieces like a "medusa" wig comprised of hundreds of robotic snakes. Various shape-memory alloys, electroluminescent materials, and the like, may be used within the scope of this invention.

Additionally, auto darkening eyeglasses may be used to convey a "don't bother me" affect. Auto darkening screens in eyewear or other vehicles for communication such as cars, boats, and buildings, can be used as well.

Likewise a mediated reality environment can convey the affect and the sensing can be done therein, or one or both can be brought into a virtual environment.

FIG. 6c depicts an Antail™ embodiment of the invention. An antenna tail is moved by a motor 610. The Antail 610A initially rests in a downward position of less efficacy and less visibility. When the network connection is aroused the Antail stands erect in position of greater efficacy and greater visibility which is shown in the drawing FIG. 6c as Antail 610E.

The motor 610 is responsive to an output from processor 130. Processor 130 also attains its network connection through Antail 610A. Processor 130 is responsive to an input from an input device such as EEG120 or a camera 120C.

When user 110 is threatened her Antail stands up to deter would-be attackers. The fact that the Antail is controlled by EEG which is an inherently unreliable medium, only helps to add some deniability. When asked "did you stand your tail up at me?" she can say "it has a mind of its own". In this sense the tail can be presented as a playful emoticon that has a "mind of its own" (e.g. is unreliable) so that it is not seen as an overt act of aggression or arousal.

In a more playful sense, when the EEG 120 pickups up on a high degree of visual saliency, processor 130 then requests more visual bandwidth to archive images from camera 120C faster. This need for bandwidth causes an erection of Antail 610A to position Antail 610E which happens whenever interesting visual subject matter is present. Thus if user 110 sees a Person of Interest, she is aroused and her antenna stands up, but this may happen often accidentally enough to become a cute conversation piece. For example, the user 110 might have seen something else in her visual field of view at the same time as another person walked by. This randomness gives the apparatus some useful deniability and renders it like the fool of the King's court who can be excused for random utterances, and can therefore speak truth without risking offending anyone.

Indeed, due to the number of incidents in which police themselves are the assailants (e.g. police seizing or smashing journalist's cameras, or the like), the apparatus can provide a safe defense against attack by police who would otherwise be offended (and may become violent) by an overt act of documentary practice.

More generally, the apparatus of the invention, in this embodiment, includes an affect indicator (e.g. like the tail that can fall limp during a mode of less affect and stand erect during a mode of higher affect), an affect sensor (e.g. the EEG headset or brainwave electrodes, or the like), and a processor responsive to an output from the affect sensor, with the affect indicator being responsive to an output from the processor. Preferably the affect indicator provides at least one other function, and has at least two states: a position of lesser efficacy that corresponds to a position indicative of a lesser affect, and a position of greater efficacy that corresponds to a position of greater affect.

In another embodiment, for example, the affect indicator might be camera 120C itself, rather than (or in addition to) Antail 610. The camera in this embodiment can "stand up" (e.g. raise upwards, for example) and be more visible to other people while at the same time become more effective at taking pictures. When user 110 is visually aroused, for example, or startled, her camera or cameras stand erect and capture images more clearly while also expressing this affect to potential attackers or in a playful sense simply to other people. When she is less aroused, her cameras droop down into her hairstyle and are partially obscured by her hair. Perhaps the cameras can still record images, but they may be less effective in doing so.

This embodiment of the invention may also be used on or in an automobile, or building, for example. For example, with the invention, a camera on the roof of a car can "look" at an annoying driver next to you, and capture video of the annoying or dangerous driver in a way that expresses affect to the driver of the other car.

In other embodiments of the invention, user 110 has an affect indicator that exists purely (or additionally) in cyberspace or cyborgspace or some kind of mediated reality. When persons view her through their cameraphones they can see her emotional state indicated by these online affect indicators. Thus a sort of game or conversation piece or informal kind of interaction can take place in an online world.

Participants in the online world can choose to see or be seen in a sense of affect expression that does not require they wear any special apparatus other than perhaps some simple kind of sensor such as the brainwave sensor of EEG 120 or the like.

For example, another participant 620O wearing special eyeglasses 620E can see a virtual rendition of a tail on user 110 rise and fall in accordance with some parameter such as visual salience or arousal of the visual cortex, or certain other brainwave or cardiographic or respiratory response, or the like.

The motorized or vibrotactile embodiments of the invention can be used in various ways for various purposes. For example, physiotherapy applications might include a massage chair that uses collaboration to allow couples to relax together and massage each other (e.g. rub each other's backs in cyberspace, across disparate geographical boundaries).

When the frequencies of multiple tactuators in this invention operate in the ratio of small whole numbers, a nice musical sound results. More generally, some form of acoustic feedback is useful. Musical sounds that play in the same key as the motor vibrations are also useful. In one embodiment of the invention there is a tactuator that generates songs that can be heard through bone conduction while brushing teeth. In other embodiments of the invention there are separate sounders that may also play in key with the motor vibrations, and the motor vibrations move through a song as the root note of each chord in the song.

In other embodiments multiple motors are used to synthesize sound waves by superposition. In a preferred embodiment one motor can play the root note of each chord while a separate sounding device, speaker, geophone, or the like plays the melody. In other embodiments, one or more motors play bass notes while a separate speaker or the like plays other musical parts of an arrangement that is responsive to brainwaves.

In this embodiment of the invention the TUI and RUI may be space-division multiplexed, e.g. they may comprise a heating element array that has some elements detectable by the transmitient and some elements detectable by the recipient. Alternatively the TUI and RUI may be one-in-the same. For example, the implement may have a single heating element that is detectable by the patient and the dentist or by the parent and the child. In this way the patient can feel the TUI signal which is the same as the RUI signal.

There are merits in simplicity of the TUI being the RUI, but there are also certain aspects of some embodiments of the invention where the flexibility of having the TUI and RUI separate make sense.

In the foregoing the TUI and RUI of the invention were presented as spatially separated, when separated. But the separation, if desired, can be spatial or temporal, for example.

For example, the invention can take the form of a playfully fun and silly hat with a directional speakermic (speaker and microphone) shaped like a dish antenna. The speakermic is on a swivel with servos to control azimuth and elevation. Acting as a microphone it is the environmental sensor. Thus it can "listen" to various sounds in the environment. As it senses various sounds in the environment it supplies this sensed data to the processor 650 which also monitors EEG 120 of user 110 to determine whether or not the user is annoyed or pleased or interested or disinterested, or the like.

The speakermic then "responds" to the sensed sound. For example, if processor 650 determines that the user is annoyed, an inference engine algorithm running in the processor attempts to correlate this annoyance with the sensed sound. The sensed sound might have a particular rhythm or periodicity or other temporally-varying attribute that makes it easily correlatable. An annoyance correlator then makes an inference as to the degree of cause the particular sound is making to the annoyance of the user. An annoyance attribution table is constructed in processor 650 to relate the annoyance to each sensed sound and direction of arrival of the sound, and the like. A support vector machine or other simple learning algorithm maps out the space by way of a spatial annoyance map, so as to define annoying sounds by their direction of arrival, or the like.

Suppose, for example, the annoying sound is that of a poorly-played guitar. Guitars are commonly sold at grocery stores and department stores. For example, Walmart stores often have several different kinds of guitars for sale as impulse-buy items right at the checkout counter. One store had seven different kinds of guitars right at the cash registers, among the items placed there for people to buy as last-minute purchases. Accordingly a number of non-musicians buy these extreme low-cost guitars and begin to self-teach and play in public, etc., while learning (e.g. "strum, plunk, thump, clunk . . . ").

Let us suppose, for example, that the user of the invention encounters such an annoying sound that has a steady easily-detectable rhythm that can be measured using an annoyance rhythm correlator. Periodic patterns can be linked to brain state or brainwave activity by known evoked potentials detection algorithms. Thus periodic disturbances can be correlated through signal averaging as well as more modern techniques well known in the art.

Suppose therefore that the "ear" (speakermic) swivels around on its turret and points to find the annoying guitar sound. Processor 650 thusly identifies the sound as annoying to the user, and an affects generator is actuated. An affects generator is an effects generator that is aimed at expressing affect, such as this annoyance. Processor 650 reads the annoying guitar sound, and then accentuates the aspects of it that are annoying. For example, the affects generator frequency-shifts the sound to make it a little bit out-of-tune. The processor waits for a pause in the sound, and then the speakermic momentarily becomes a speaker, and plays back an annoyance-processed version of the sound to convey to the guitar player the annoyance that the sound has caused. The resulting annoyance burst is, for example, a brief dischordant blast of sampled guitar sound, a little out-of-tune.

The algorithm running on the processor 650 that generates this annoying sound is herein called an annoyance burst generator or an annoyance affects generator. It generates a burst of annoyance based activity and in this example, it blasts that out during a brief pause in the guitar sound source.

In other embodiments the environmental sensor and affector may be shoulder-mounted, e.g. 2 speakermics, one on each epaulet of a garment, or various earlike devices that rise and point to a sound source to express to others that they have been heard. The affect generator may be the mere sight of the ear or ears turning toward the sound, or it may be an annoyance burst or other signal sent back to the sound source. The affect generator may be separate from the environmental sensor, or it may be the environment sensor. For example, a separate speaker and microphone may be used, and only one of them need be affectively directional. By affectively directional I mean that its direction is visible to others, and thusly this directional "gaze" is its way of expressing the affect, or is, in fact the affect generator.

In situations where it produces sound or other stimulus, that stimulus may itself be the affector. Thus the affects generator may be its output, such that it need not have a visible directionality.

There is a need for music sharing in various new ways, as we often see couples walking along the street where each person is wearing one of the earphones of a stereo music player. Miniaturization has taken away the speakers of the old "transistor radio" that previously allowed people to listen to the same music. Thus affective music sharing and synchronization is beneficial for all. The invention can for example, pickup music from others who have subscribed to a music sharing world, and create a virtual world in which the affector is a sharing of the music.

FIG. 6d depicts an apparatus in which the TUI and RUI are temporally separable, if desired, and in which the affector is sound output rather than a visible directionality. A processor 650 has an array 650A of sensors such as, for example, a microphone array which can be steered to listen in various directions by way of directionality 650D. This directionality allows it to receive sound from a noise source such as noise source 650N. The upper half of FIG. 6d illustrates microphone array 650A operating as an environmental sensor at, at some time such as t_1, said time denoted as time 650T1. The lower half of FIG. 6d illustrates array 650A acting as an affector to produce sound such as an annoyance burst, at time t_2, denoted time 650T2.

The invention is not limited to annoyance. For example, sounds that I find pleasing may be "reflected" back to their environment in a supportive way. If I hear a song I like, the parts I like are sent back. When someone near me sings a song that brings pleasure to my heart, I reflect back to it with melodious and harmonious responses akin to "jamming". In this way if I'm not paying attention my WearComp (wearable computer) responds on my behalf and my WearComp "sings along" with the sounds around me that please me.

FIG. 6e denotes an automotive embodiment, but the invention may of course also take the form of smart clothes, smart buildings, smart boats, airplanes, or other body covering. The clothes or car or boat or the like is just then an extension of the user's own mind and body.

Ideally the entire surface of the automobile or other body covering is an affector display and environmental sensor camera or the like.

Practically, however, such a complete mediated reality would not be easy to attain, unless at high budget such as to make an invisibility suit or invisibility shield that would be entirely affector and sensor.

More likely we might have a few mediation zones such as affector 690A which is a projection screen on the outside of a vehicle 690. For example the vehicle or other vessel may be white and the screens sculpted into it to match so that when not affecting, the vehicle is all white, and when affecting, the affector appears to hover within this whitespace.

An environmental sensor 690s may take the form of a camera that can "see" (that has a field of view of) that which is beyond the vehicle 690. The vehicle may be an outfit for example (e.g. clothes) with display as affector 690A and camera as sensor 690s.

The vehicle might form a reflectionist rendition of others, as per the article ""Reflectionism" and "Diffusionism": New Tactics for Deconstructing the Video Surveillance Superhighway" by author Steve Mann, published in Leonardo, Volume 31, Issue 2 Apr. 1998, pp 93-102.

For example, the vehicle might display the face of a person looking at it. Let us suppose, for example, that someone is getting to close to me and thus invading my personal space. My processor 650 receives input from environmental sensor 690s as well as EEG sensors or other affect or physiological sensors on my own body. A classification algorithm thus correlates my own physiological response with this data and when there is a strong correlation, produces affects. The garment or other vehicle 690 around me thus, for example, generates a picture of the person seen on camera 690s and displays it to that person by affector 690A.

Thus a potential assailant invading the body space or corporeal envelope of the user is presented with an image of himself, much like the potential shoplifter sees his own image on the TV screens often placed at department store entrances to remind shoppers that they are under surveillance.

In this example, my invention reminds potential perpetrators that they are under surveillance.

The invention can be used in garments or in cars. For example, a person invading the personal space of a motorist can be presented with an image of their own vehicle reflected on screen 690S. In this way a person following too closely will see their own car, and can see that their license plate is visible, on the camera-displayed image that might be labeled with "image captured and transmitting . . . ". Face recognition or optical character recognition can display the name of the person or their license plate number for example. Thus when someone stands too close to me they will see a message like "John, don't stand so close to me"

displayed on display affector 690A. Optical character recognition of the license plate with reverse lookup of the name corresponding thereto can also be used, e.g. "A car registered John Doe is following me too closely and invading my personal space bubble".

A camera dome fitted on the top of vehicle 690 may also be used. For example, if vehicle 690 is an outfit, the top may be a hat. If vehicle 690 is a car, the top may be the roof of a car. A magnetic mount dome camera with visible turret may be placed thereupon and it turns and "looks" at drivers who are driving dangerously. In some embodiments it is anthropomorphised so as to resemble a human face or eye, and it may wink, blink, or "scowl" at others.

Thus the invention functions as a Personal Safety Device (PSD) to deter stalking, intimidation, invasion of personal space, dangerous driving, and the like.

But the invention is not limited to negative affect. It may also express positive affect, for example, visually, as with the previous audio based embodiment. A visual situation that brings pleasure is reflected back using a pleasing image derived from the source of the pleasantness.

For example, the vehicle 690 might be a shirt having lights in it that are an affects generator to message to someone in the environment. If the person standing right in front of my pleases my heart, my heart might throb through the lights (lights display my ECG) to let that person know they've brought pleasure to my heart.

FIG. 7 is a diagram showing a hot tub embodiment. In a hot tub 710, water jets 720 are supplied by a pump 720P through a hydraulophone 720H or other similar water feature. Processor 550 (not shown) drives pump 720P in response to a degree of concentration, relaxation, or the like, while a user 110 (not shown) sits in the tub and is presented with a corporate logo such as logo 730 "WATER MATTERS™" reflected in the waterline, or a corporate logo "MATERLINE™" at the waterline.

As interesting optical properties of the waterline are controlled by brainwaves, the brainwaves make water waves, by way of pump 721P and manifold 721M, the user is entrained to concentrate on these effects, in much the same brainstate induced by television.

The desired brainstate is entrained while the user concentrates on the logos, etc.

In another embodiment, the hydraulophone jets 720 rise and fall with brainstate, and illumination in the jets is responsive to brainstate.

A multi-user game is also possible. For example, users engage in a collective stream of deconsciousness, relaxation, meditation, or the like. In one embodiment, users concentrate together to raise the water jets. An alpha wave consolidator functions like a soft "and" gate (Boolean logic) or a summation, so that when everyone is in a meditative state, the jets rise, creating the feeling of collective consciousness.

The hot tub can also use multiple pump motors to introduce aspects of the invention that are musical or tactile in various ways previously described. For example, multiple motors can be used to synthesize beat frequencies that create a throbbing effect or beat effect to follow the beat of a musical melody or to follow the natural rhythms of the mind and body of users or participants in or around the tub.

The hot tub can also have addressable arrays of affectors such as an array of energy modulator jets that can vary their temperature, pressure, and other attributes to convey an affect to a spa participant. Multiple spa participants in the same tub, or in different tubs at different geographical locations, can share the waters. For example, an array of jets can be a TUI to one person and an RUI to another, while at the same time being sensors by way of being hydraulophonic or having some kind of sensory capability such as a fluid user interface as outlined in U.S. Pat. No. 7,551,161, "Fluid user interface such as immersive multimediator or input/output device with one or more spray jets", by Mann, filed 2005 Dec. 14$^{th}$ with priority document of corresponding Canadian Patent 2499784 "WET USER INTERFACE OR LIQUID USER INTERFACE WITH ONE OR MORE SPRAY JETS OR BODIES OF WATER", filed December 2004.

Other sensors can be used. For example a satisfactory RUI is a heart monitor. The processor reads from the heart monitor and throbs the water jets in response to the heart. Two bathers at opposite ends of the same tub, or in different tubs possibly in different countries can bathe heart-to-heart (e.g. where one's heartbeat throbs the other's water jets). For example, one person's tub is or contains an affects generator for the other person's sensor, and possibly vice-versa as well.

In other embodiments, water showers are modulated as Rainwavesj™ that derive from brainwave controlled valves or pumps. Water faucets and showers thus also fall within the scope of the invention.

Some embodiments of the invention may be handheld. Others are worn. Others are implanted. There are also various combinations possible. For example, portions of the apparatus may be permanently attached and other portions may be lesser attached.

FIG. 8 depicts a ThinkingCap™) having a portion 800 that permanently attaches to the skull of a user. A skull cap mesh 810 forms a fine grid for the head. The hair is shaved off, and after the device is installed, the hair grows through the mesh holes. In the interim or in combination, a hairpiece may be part of the apparatus. Eyeglass frames 820 form part of the apparatus. In this way the eyeglasses are held securely in place by the mesh 810 and the frames 820 and additionally there is an occipital lobe comfort band 830 that goes around the back of the head and picks up a connection to one or more DermaPlant™ or indwelling electrodes for the visual cortex. The permanent portion 800 may have various other sensors on it. For example, earlobe pickups 821 and nosebridge pickups 822 help to read more data. Earlobe pickups make good ground points or reference points and can pickup where there is very little EMG noise, for example. The point where eyeglass frames 820 touch the mastoid also form electrical contacts. Particular attention is made to the structure of the eyeglass frames 820, whether simply part of the skull cap, or separate but attached, they spring and touch the side of the face, and contain electrode arrays that read out from the side of the face. The large number of contact points of numerous electrodes all around the face read out affective (emotional) state of the user and also various facial expressions can be read. Nosebridge pickups can also help pickup EOG (Electro Occulo Gram) eye movement, or the like. Occipital lobe box 831 contains and protects occipital lobe readout and interface devices such as a neural network reading the occipital lobe. It also houses a rear-looking camera as part of the Personal Safety Device (PSD). This need not be a high resolution camera but simply a miniature camera that might capture the face of an attacker sneaking up behind.

This embodiment may also include various body piercings such as nose, head (similar to hairpiece attachments) and the like. In this way it is, at least in part, a permanent fixture for which removal is non-negotiable, e.g. on the "will-not, may-not, cannot continuum" it falls to the "cannot" side of this continuum, such as to make compliance with a perpetrator impossible rather than the victim seeming to be uncooperative.

There are mount points 850 that can accept various task-specific devices. For example, a WeldView™ HDR (High Dynamic Range) camera may be fitted to the side of the headpiece to look out through a welding helmet as a seeing aid for high contrast subject matter such as seen during electric arc welding. As a safety precaution the electric welding apparatus can look for simultaneous high alpha and high beta brainwave activity before starting up (e.g. to make sure the user is fit to safely use the machine). Upon such safety check and the machine starts, the user then can see through camera 840 the electric arc of the weldment, and surrounding material as well.

Various different kinds of attachments and different kinds of seeing aids can thus be fitted to a BrainBus™ which is to the brain as the USB (Universal Serial Bus) is to a computer. In this way the user can plug various things into their brain. A wearable computer 860 wirelessly connects to the BrainBus as well as one or more peripherals like camera 840, or the like.

Additionally, the BCI renders objects and devices, such as the electric arc welder, acting as if true extensions of the mind and body, e.g. as if they were body parts of the user.

The permanent portion 800 has various sensors and effectors on it. The result of having it always present on the body is that the mind learns how it works and over time, it becomes useable and like a part of the body. By constant exposure to some aspects of the BCI and its biofeedback or Humanistic Intelligence feedback loops, the user's brain begins, over time, to subsume the ThinkingCap™ into the prosthetic territory as if it were a third hemisphere of the brain. Then when devices are plugged into the BrainBus™ of points 850, they are much more readily learned and used as if true body parts.

In one embodiment of this invention, there is a continuous capture of personal experiences with EEG, so that images, for example, can be searched based on EEG information like visual salience. For example, a person can record their entire life and then that data can be correlated to brainwaves. This may, for example, allow lifelogging (lifelong CyborGLOGGING) data to be searched automatically.

Various forms of data collection such as camera-switching (between rear-facing camera in occipital box 831 and forward camera 840, for example) can be automated.

Various arrays of cameras, microphones, and other sensors are switched and allocated automatically based on eye gaze, brain state, etc.

Thus the apparatus does simple things like focus where you look, steer the beam of a microphone array to where you look, etc., while also using visual salience and visual arousal information from the occipital lobe to guide this process during capture, as well as to search through the data later on.

A doctor might, for example, assist a patient by solving a work-related stress problem by looking at EEG and correlating it with activity.

Wearable computer 860 may also include ECG (Electro Cardio Gram) hookup so a video Holter monitor is possible that includes EVG and EEG to help determine causes of stress and avert potential heart failure.

A doctor can see what might have caused heart stress, by reviewing the video and also the visual arousal EEG information and visual salience EEG information and correlating that to ECG data such as heart beat arrhythmia.

FIG. 9 depicts a variation of the ThinkingCap 910 in which three implantable devices, e.g. internal devices 901 are shown. These devices remain totally inside the head 900 of the user. The ThinkingCap 910 has three external devices 911.

The external devices 911 transmit electrical power to the internal devices 901 over a very short distance. This power transmission is wireless so that there is no need for wiring emerging from the body and thus passing through the skin of the user. The external devices 911 also have a wireless data communications link to the internal devices 901. The ThinkingCap 910 may be permanently attached in some embodiments, semipermanently attached in other embodiments, or may even be removable in other embodiments.

Modifications will be apparent to those skilled in the art and, therefore, the invention is defined in the claims.

What is claimed is:

1. A brainwave actuated apparatus, comprising:
a brainwave sensor for outputting brainwave signals;
an effector responsive to an input signal to provide biofeedback to a user;
a controller operatively connected to an output of the brainwave sensor to receive the brainwave signals and a control input to the effector, said controller adapted to:
determine brainwave characteristics of the brainwave signal output by said the brainwave sensor, the characteristics indicative of a brain state of the user;
determine that the brain state of the user is a sleep state; and
derive a control signal to provide biofeedback stimulus by the effector based at least in part on the brain state, wherein the control signal is configured to provide the biofeedback stimulus to entrain a desired brain state and the biofeedback stimulus is in a range of desired brainwave entrainment and phase locked with the brainwave characteristics of the user, in a phase locked loop.

2. The apparatus of claim 1, wherein the biofeedback stimulus includes one or more of sinusoidal signals of pure tone, spread spectrum excitation, or other arbitrary periodic or quasi-periodic signals.

3. The apparatus of claim 1, where biofeedback stimulus includes binaural tones.

4. The apparatus of claim 1, wherein the biofeedback stimulus is one or more of a tactile stimulus, a temperature stimulus, an audio stimulus or a visual stimulus.

5. A computer-implemented method comprising:
determining brainwave characteristics of brainwave signals output from a brainwave sensor, the characteristics indicative of a brain state of a user;
determining that the brain state of the user is a sleep state; and
determining a control signal to provide a biofeedback stimulus from an effector to the user based at least in part on the brain state,
receiving additional brainwave signals tuned to a range of frequencies corresponding to the biofeedback stimulus for brainwave entrainment, wherein the biofeedback stimulus is output in a phase locked loop with the brainwave signals tuned to the range of frequencies.

6. The method of claim 5, further comprising: outputting an indication of additional brainwave signals that correspond to the range of frequencies corresponding to the biofeedback stimulus.

7. The method of claim 6, wherein the indication is a biofeedback signal.

8. The method of claim 5, further comprising: determining that the brain state is an awakening state based at least in part on detecting a transition of a dominance of theta brainwaves to a dominance of alpha brainwaves.

9. The method of claim 5, further comprising:
   determining that the brain state of the user is a REM sleep state; and
   providing the stimulus from the effector to awaken the user.

10. The method of claim 9, further comprising: accepting input that describes a dream, wherein the characteristics are indicative of an emotional state.

11. The method of claim 9, further comprising: providing a further biofeedback stimulus from the effector for entrainment to re-sleep the user.

12. The method of claim 9, further comprising: detecting non-movement of a body part of the user, and, determining a further control signal, based at least in part on the detected non-movement, to provide a further biofeedback stimulus from the effector for entrainment to re-sleep the user.

13. The method of claim 5, further comprising: detecting a transition from an awake state to the sleep state.

14. The method of claim 5, further comprising: detecting a transition from the sleep state to an awake state.

15. The method of claim 5, wherein the determining that the brain state of the user is the sleep state is based at least in part on one or more of a heart rate of the user or a motion vibration sensed from the user.

16. A non-transitory computer readable medium comprising a computer readable memory storing computer executable instructions thereon that when executed by a computer cause the computer to perform the method of claim 5.

* * * * *